US012558342B2

(12) United States Patent
Kavakli et al.

(10) Patent No.: US 12,558,342 B2
(45) Date of Patent: Feb. 24, 2026

(54) 2-[2-({12,12-DIMETHYL-4-OXO-6-PHENYL-3,11-DIOXATRICYCLO [8.4.0.0,2,7]TETRADECA-1,5,7,9-TETRAEN-8-YL}OXY)ACETAMIDO] BENZAMIDE AND DERIVATIVES AS INHIBITOR OF CLOCK:BMAL1 INTERACTION FOR THE TREATMENT OF CIRCADIAN RHYTHM DISEASES AND DISORDERS

(71) Applicant: KOC UNIVERSITESI, Istanbul (TR)

(72) Inventors: Ibrahim Halil Kavakli, Istanbul (TR); Metin Turkay, Istanbul (TR); Yagmur Umay Doruk, Istanbul (TR); Darya Yarparvar, Istanbul (TR)

(73) Assignee: KOC UNIVERSITESI, Istanbul (TR)

( * ) Notice: Subject to any disclaimer, the term of this patent is extended or adjusted under 35 U.S.C. 154(b) by 905 days.

(21) Appl. No.: 17/785,970

(22) PCT Filed: Dec. 16, 2019

(86) PCT No.: PCT/TR2019/051082

§ 371 (c)(1),
(2) Date: Jun. 16, 2022

(87) PCT Pub. No.: WO2021/126096

PCT Pub. Date: Jun. 24, 2021

(65) Prior Publication Data

US 2023/0078642 A1 Mar. 16, 2023

(51) Int. Cl.
*A61K 31/352* (2006.01)
*A61P 25/00* (2006.01)

(52) U.S. Cl.
CPC ............ *A61K 31/352* (2013.01); *A61P 25/00* (2018.01)

(58) Field of Classification Search
CPC .................................................... A61K 31/352
See application file for complete search history.

(56) References Cited

FOREIGN PATENT DOCUMENTS

| | | | |
|---|---|---|---|
| WO | 2018132383 | A1 | 7/2018 |
| WO | 2018165037 | A1 | 9/2018 |

OTHER PUBLICATIONS

Tsuyoshi Hirota, et al., High-Throughput Chemical Screen Identifies a Novel Potent Modulator of Cellular Circadian Rhythms and Reveals CKla as a Clock Regulatory Kinase, PLoS Biology, 2010, pp. 1-14, vol. 8, Issue 12.

Yasushi Isojima, et al., CKIε/δ-dependent phosphorylation is a temperature-insensitive, period-determining process in the mammalian circadian clock, PNAS, 2009, pp. 15744-15749, vol. 106, No. 37.

Tsuyoshi Hirota, et al., Identification of Small Molecule Activators of Cryptochrome, Science, 2012, pp. 1094-1097, vol. 337, No. 6098.

Sung Kook Chun, et al., Identification and Validation of Cryptochrome Inhibitors That Modulate the Molecular Circadian Clock, ACS Chemical Biology, 2014, pp. 703-710, vol. 9.

Yan Hu, et al., Selenium is a modulator of circadian clock that protects mice from the toxicity of a chemotherapeutic drug via upregulation of the core clock protein, BMAL1, Oncotarget, 2011, pp. 1279-1290, vol. 2, No. 12.

Nian Huang, et al., Crystal Structure of the Heterodimeric Clock:BMAL1 Transcriptional Activator Complex, Science, 2012, pp. 189-194, vol. 337, No. 6091.

Brian E. Mcintosh, et al., Mammalian Per-Arnt-Sim Proteins in Environmental Adaptation, Annual Review of Physiology, 2010, pp. 625-645, vol. 72.

Yuliya V. Dubrovsky, et al., Deficiency of circadian protein Clock reduces lifespan and increases age-related cataract development in mice, Aging, 2010, pp. 936-944, vol. 2, No. 12.

H. A. Mansour, et al., Association study of eight circadian genes with bipolar I disorder, schizoaffective disorder and schizophrenia, Genes, Brain and Behavior, 2006, pp. 150-157, vol. 5.

Colleen A Mcclung, Clock genes and bipolar disorder: implications for therapy, Pharmacogenomics, 2007, pp. 1097-1100, vol. 8, No. 9.

Caroline M. Nievergelt, et al., Suggestive evidence for association of the circadian genes PERIOD3 and ARNTL with bipolar disorder, Journal of Medical Genetics Part B: Neuropsychiatric Genetics, 2006, pp. 234-241, 141B(3).

Martha Hotz Vitaterna, et al., The mouse Clock mutation reduces circadian pacemaker amplitude and enhances efficacy of resetting stimuli and phase-response curve amplitude, PNAS, 2006, pp. 9327-9332, vol. 103, No. 24.

James C. Phillips, et al., Scalable Molecular Dynamics with NAMD, Journal of Computational Chemistry, 2005, pp. 1781-1802, vol. 26, No. 16.

William Humphrey, et al., VMD: Visual Molecular Dynamics, Journal of Molecular Graphics, 1996, pp. 33-38, vol. 14.

Garrett M. Morris, et al., AutoDock4 and AutoDockTools4: Automated Docking with Selective Receptor Flexibility, Journal of Computational Chemistry, 2009, pp. 2785-2791, vol. 30, No. 16.

(Continued)

*Primary Examiner* — Yong S. Chong

(74) *Attorney, Agent, or Firm* — Bayramoglu Law Offices LLC

(57) ABSTRACT

A 2-[2-({12,12-dimethyl-4-oxo-6-phenyl-3,11-dioxatricyclo [8.4.0.0,2,7]tetradeca-1,5,7,9-tetraen-8-yl}oxy)acetamido] benzamide compound and related derivatives, as well as the use thereof in the preparation of a medicament for treatment and/or prevention of diseases or disorders associated with the circadian rhythm are provided. The compound of the invention is a CLOCK-binding small molecule and also an inhibitor of CLOCK:BMAL1 interaction, and is therefore useful, as pharmaceutical agent, especially in the treatment and/or prevention of disorders associated with the circadian rhythm.

3 Claims, 21 Drawing Sheets

Specification includes a Sequence Listing.

(56) References Cited

OTHER PUBLICATIONS

Christopher A. Lipinski, Drug-like properties and the causes of poor solubility and poor permeability, Journal of Pharmacological and Toxicological Methods, 2000, pp. 235-249, vol. 44.

Roman V. Kondratov, et al., BMAL1-dependent circadian oscillation of nuclear Clock: posttranslational events Induced by dimerization of transcriptional activators of the mammalian clock system, Genes & Development, 2003, pp. 1921-1932, vol. 17.

Magdalena A. Biernat, et al., A Baculovirus Photolyase with DNA Repair Activity and Circadian Clock Regulatory Function, Journal of Biological Rhythms, 2012, pp. 3-11, vol. 27, No. 1.

Yagmur Umay Doruk, et al., A Clock-binding small molecule disrupts the interaction between Clock and BMAL1 and enhances circadian rhythm amplitude, Journal of Biological Chemistry, 2020, pp. 1-24.

2-[2-({12,12-DIMETHYL-4-OXO-6-PHENYL-3,11-DIOXATRICYCLO [8.4.0.0,2,7]TETRADECA-1,5,7,9-TETRAEN-8-YL}OXY)ACETAMIDO] BENZAMIDE AND DERIVATIVES AS INHIBITOR OF CLOCK:BMAL1 INTERACTION FOR THE TREATMENT OF CIRCADIAN RHYTHM DISEASES AND DISORDERS

CROSS REFERENCE TO THE RELATED APPLICATIONS

This application is the national phase entry of International Application No. PCT/TR2019/051082, filed on Dec. 16, 2019, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBAP222_Sequence Listing.txt, created on Jun. 14, 2022, and is 11,986 bytes in size.

TECHNICAL FIELD

The present invention discloses and claims 2-[2-({12,12-dimethyl-4-oxo-6-phenyl-3,11-dioxatricyclo [8.4.0.0,2,7] tetradeca-1,5,7,9-tetraen-8-yl} oxy) acetamido] benzamide (formula I) as CLOCK-binding small molecule and inhibitor of CLOCK:BMAL1 interaction, and method of using said compound formula I for treating disorders including aging, mood disorders, sleep disorders and diseases related with reduced circadian amplitude. Pharmaceutical compositions comprising formula I and methods for the preparation of formula (I) are also disclosed and claimed.

BACKGROUND

The circadian clock generates a 24-hour rhythm through which physiology and behavior adapt to daily changes in the environment. Many biological processes like hormone secretion, and sleep-wake cycles are controlled by the circadian clock. Therefore, an innate malfunctioning of the circadian clock or a shift between internal circadian rhythm and the external environment can cause various pathologies. Sleep disorders, altered metabolism, obesity, diabetes, mood disorders, cancer and cardiovascular diseases are all linked to an abnormal circadian rhythm. Also, a decrease in the robustness of the circadian rhythm (amplitude decline) is correlated with different pathologies and chronic diseases such as mood disorders and metabolic diseases. Aging is also associated with dampened amplitude and imperfect timing of the circadian rhythm and therefore a weakening of many clock-controlled physiological processes.

The mammalian circadian clock is based on a positive and negative transcription/translation feedback loop (TTFL) in which CLOCK and BMAL1 proteins act as transcriptional activators of Cryptochrome (Cry) and Period (Per) genes, which encode proteins that repress CLOCK-BMAL1 with a periodicity of ~24 h. In the positive arm of the loop, CLOCK and BMAL1 heterodimerize and positively regulate the expression of clock controlled genes including Per and Cry genes. In the negative arm of the loop, the PER: CRY complex along with casein kinase IA translocates into the nucleus, interacts with CLOCK:BMAL1, and inhibits the transcriptional activity of CLOCK:BMAL1, therefore repressing the transcription of Per and Cry and other clock controlled genes. Once PERs and CRYs are degraded, the repression is relieved and a new cycle starts. The second feedback loop consists of RORs and REV-ERBs, which are expressed under the control of CLOCK:BMAL1 and activate and repress the transcription of Bmal1, respectively. A robust and precise rhythm is not generated unless the amount of clock proteins, their localization and their activity are precisely regulated; a process in which several post-translational modifications is involved.

Without a robust and well-aligned circadian rhythm, organisms cannot adapt to environmental changes adequately deafening the evolutionary purpose of the circadian clock. To modify a disrupted circadian rhythm, small molecules are of great priority due to their reversible and time and dose-tunable effects. So far, unbiased screening based on phenotypic changes in the circadian rhythm of reporter cells have resulted in the discovery of multiple clock modulating small molecules with various circadian phenotypes (Hirota et al., 2010; Isojima et al., 2009). Among these compounds, KL001 binds to CRY and stabilizes it (Hirota et al., 2012). Enhancers of CLOCK:BMAL1 transcriptional activity, and a molecule that augments CRYs repression activity have been detected in high-throughput screening studies utilizing mechanistic approaches (Chun et al., 2014; Hu et al., 2011). Targeting nuclear receptors and protein kinases involved in the circadian clock mechanism has resulted in the identification of different ROR agonists/antagonists, REV-ERB agonists and kinase inhibitors.

In the international patent document WO2018132383A1, small molecule agents that disrupt CRY1-CLOCK-BMAL1 ternary complexes are disclosed. According to this invention, these disrupting agents bind to the secondary pocket of CRY1 and in this way inhibit interaction between the secondary pocket and the CLOCK PAS-B domain. Agents of interest herein are small molecules, polymer, peptides, polypeptides.

Another effective method to identify small molecules that perturb a biological system is structure-based design. Since the crystal structures of clock proteins are now available, this approach can lead to identification of clock modulating compounds targeting clock proteins. The crystal structure of CLOCK:BMAL1 heterodimer reveals that similar domains of CLOCK and BMAL1 (bHLH, PASA, and PAS-B) interact with each other and provide three protein-protein interfaces (Huang et al., 2012). Different hollows and clefts are present on the surface of each protein, allowing them to interlock to make a stable interaction. Containing a PAS domain, per se, makes CLOCK a druggable target because PAS domains, as internal sensors of living cells, are capable of binding different cofactors (McIntosh, 2010).

Many physiological variables require a robust circadian clock for their proper function. Disturbances in the circadian clock can result in various metabolic diseases and accelerated aging. There is a need for a circadian rhythm controlling molecules and compositions capable of improving circadian rhythm dysfunctions, in particular, a circadian rhythm controlling molecules or compositions capable of amplifying the amplitude of circadian rhythm. It has therefore become increasingly interesting to identify small molecules that can specifically modulate regulatory core clock proteins since they have the potential to manage these diseases. The CLOCK plays a central role as a transcription factor in the circadian pacemaker and makes it an attractive target for therapeutic intervention in aging, sleep disorders and mood disorders. There are evidences that CLOCK be active in circadian rhythm disorders and inactive in healthy subjects, therefore that agents which inhibit CLOCK:BMAL1 interaction be effective in treating circadian rhythm related diseases and disorders (Dubrovsky et al. 2010; Mansour et al., 2006; McClung, 2007; Nievergelt et al., 2006; Vitaterna et al., 2006). It is possible to control circadian rhythm disorders by means of inhibiting the CLOCK:BMAL1 interaction.

Despite advances in drug discovery directed to identifying inhibitors of CLOCK and/or BMAL1 protein activity, there is still a scarcity of compounds that are both potent, efficacious, and selective inhibitors of CLOCK:BMAL1 interaction. Furthermore, there is a scarcity of compounds effective in the treatment and/or prevention of disorders associated with the circadian rhythm. These needs and other needs are satisfied by the present invention.

SUMMARY

According to a first aspect of the invention there is provided a CLOCK-binding compound of formula I or pharmaceutically acceptable salts thereof.

Accordingly, a broad embodiment of the invention is directed to a CLOCK-binding compound of formula I:

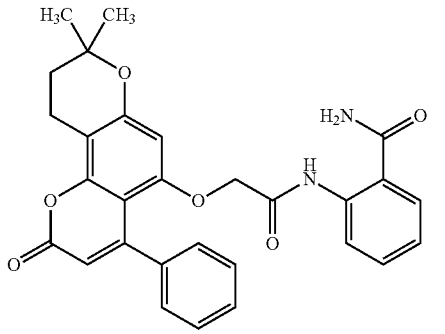 [SMILES: CC1(C)CCc2c(cc(OCC(=O)Nc3ccccc3C(N)=O)c3c(-c4ccccc4)cc(=O)oc23)O1]

The other aspect of the present invention is to provide a CLOCK-binding compound for treating and/or preventing a circadian rhythm associated diseases or disorders, wherein the compound is characterized by inhibiting CLOCK's interaction with BMAL1.

In a further aspect, the present invention relates to a CLOCK-binding compound of the invention for use in reducing strength of positive loop mediated by lowering the CLOCK:BMAL1 level in nucleus and, in turn, transcriptional activity in a mammal.

Another aspect of the present invention is to provide a CLOCK-binding compound capable of controlling circadian rhythm and amplifying circadian rhythm amplitude.

Another embodiment of the present invention relates to a method for identifying a compound for inhibiting the interaction between CLOCK and BMAL1.

The invention can be used for the preparation of a medicament useful in the treatment and/or prevention of disorders due the inhibition of CLOCK:BMAL1 interaction. Yet another objective of the present invention is to provide a pharmaceutical composition comprising a pharmaceutical carrier and a therapeutically effective amount of a compound of formula I, or a pharmaceutically acceptable salt thereof.

This object and other objects of this invention become apparent from the detailed discussion of the invention that follows.

BRIEF DESCRIPTION OF THE DRAWINGS

The present invention is illustrated in the accompanying figures wherein;

FIG. 1A shows HEK 293T cells were transfected with pcDNA-Luc and the effect of CLK8 on Luc half-life at 10, 20 and 40 μM of CLK8 were measured. The luciferase signal was monitored after CHX treatment until the luciferase signal reached a plateau. (Data are mean±s.e.m.; n=3 independent experiments).

FIG. 2A shows a chemical structure of biotinylated FORMULA I (bait). Pull down assay using whole cell lysates of FIG. 2B HEK 293T cells overexpressing Clock and Bmal1 from pSport6 plasmids, FIG. 2C shows U2OS cells. When needed FORMULA I was used as a competitor. (data are representative of 3 independent experiments)

FIG. 3A shows a chemical structure of formula I. FIG. 3B shows the best binding mode of FORMULA I to CLOCK with predicted binding energy of −8.2 kcal/mol. FORMULA I enters the hollow between the α2 helix of the bHLH domain and the HB strand of the PAS-A domain of CLOCK. FIG. 3C shows a superposition of FORMULA I and Arg126 of BMAL1 (magenta). FORMULA I and Arg126 of BMAL1 share the same binding region on CLOCK, where Phe80 plays an essential role. Also, the positively charged Lys220 on PAS-A domain of CLOCK contributes in a pi-cation interaction with FORMULA I. FIG. 3D shows a pull down assay using whole cell lysate of HEK 293T cells overexpressing CLOCK-F80A-K220A and BMAL1.

FIGS. 4A-4B show the effect of FORMULA I on the association of CLOCK and BMAL1 were evaluated by co-Immunoprecipitation experiment. Anti-FLAG affinity gel was used to precipitate FLAG-tagged CLOCK together or FLAG-tagged CLOCK-F80A-K220A mutant with BMAL1. The western blot analysis using Anti-BMAL1 and Anti-FLAG antibodies were performed to compare the association of CLOCK and CLOCK-F80A-K220A mutant with BMAL1 in samples with different concentrations of CLK8. Quantification of the blot is shown in bottom panel. The vertical axis indicating the amount of BMAL1 (normalized by CLOCK) in each sample was calculated relative to the DMSO control. FIGS. 4C-4E show unsynchronized U2OS cells were treated with 20 μM of CLK8. Control cells were treated with 0.5% DMSO. Two days later, cells were fractionated and examined by western blot analysis, where CLOCK, NPAS2, PER2, BMAL1 and CRY1 were normalized by α-TUBULIN or HISTON H3. Quantifications are shown in below. (data are mean #s.e.m.; n=5 independent experiments; western blot data is representative of 5 independent experiments); [* p-value<0.05; ** p-value<0.01;]

FIGS. 5A-5D show a time dependent analysis of core clock proteins by Western blot. (mean±SEM, n=3). FIGS. 5E-5K show a qPCR analysis of the core clock genes in a time dependent manner. (Data represent the mean±SEM, n=3 *: p<0.001 : p<0.005, *: p<0.05 versus DMSO control by one-way ANOVA Tukey).

FIGS. 6A-6D show after animals were treated with CLK8, they were scarified, and protein lysates were prepared and probed with antibodies for different core clock proteins. FIGS. 6E-6G show mice liver (n=3 for vehicle treated animals and n=5 for CLK8 treated animals) were fractionated and samples were subjected to Western blot analysis. Quantifications are shown in right panel (data are mean±s.e.m.; n=3 independent experiments for the control; n=5 independent experiments for CLK8 treated samples); [** p-value<0.01; one-way ANOVA]. FIGS. 6H-6J show the transcriptional levels of Clock, Cry1 and Bmal1 were measured with qPCR. (data are mean±s.e.m.; n=3 independent for control; n=5 CLK8 treated animals) [* p-value<0.05]. 1, 2, and 3 indicates the animal number used as control (treated with vehicle). The number indicated with 4, 5, 6, 7, 8, and 9 represents animal treated with CLK8.

DETAILED DESCRIPTION OF THE EMBODIMENTS

Figure 1A:
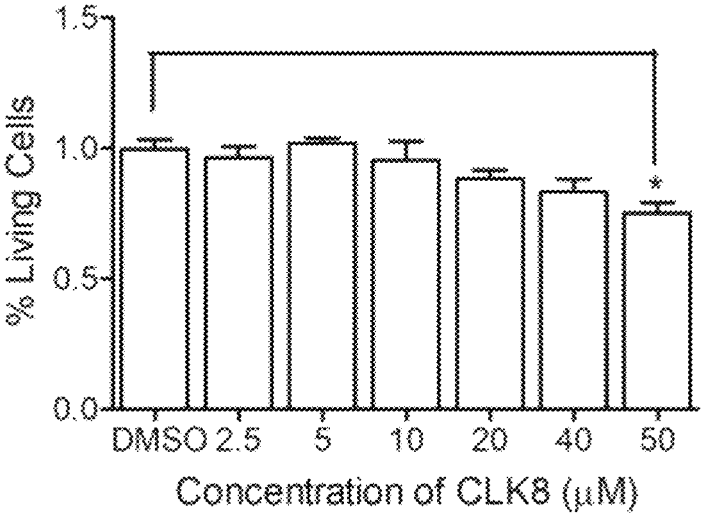
FIGS. 1A-1P are an illustration of initial screens for identification of formula I.

In the present invention, it is aimed to discover a novel CLOCK-binding small compound using a structure-based approach. As a result, the interaction of a CLOCK-binding compound with CLOCK has been predicted in silico and then demonstrated experimentally.

The CLOCK-binding compound was identified that decreases the interaction between CLOCK and BMAL1 by regulating the translocation of CLOCK into the nucleus both in vivo and in vitro.

Furthermore, it was discovered that, as a result of this interaction, the translocation of CLOCK is regulated by the CLOCK-binding compound resulting in suppression of the function thereof. A decrease in nuclear CLOCK leads the stabilization of the negative arm of the TTFL and, in turn, an enhanced the amplitude of the circadian rhythm with no change in period length.

The present invention relates to a CLOCK-binding compound (formula I).

Unless specified otherwise, the term "formula I" or "compound" or "CLK8" refers to compounds of formula I, prodrugs thereof, salts of the compound and/or prodrug, hydrates or solvates of the compound, stereoisomers, tautomers, isotopically labeled compounds, polymorphs, and derivatives of pharmacophore formula I.

It is an object of this invention to provide a CLOCK-binding compound (named CLK8) having the chemical name 2-[2-({12,12-dimethyl-4-oxo-6-phenyl-3,11-dioxatricyclo [8.4.0.0,2,7] tetradeca-1,5,7,9-tetraen-8-yl} oxy) acetamido] benzamide (IUPAC) as inhibitor of CLOCK:BMAL1 interaction and so inhibitor of transcriptional activity of CLOCK:BMAL1.

In accordance with the purpose(s) of the invention, as embodied and broadly described herein, the present invention relates to a CLOCK-binding compound, capable of inhibiting the interaction between CLOCK and BMAL1 by binding to CLOCK. In this regard, the invention relates to a compound having the following formula I:

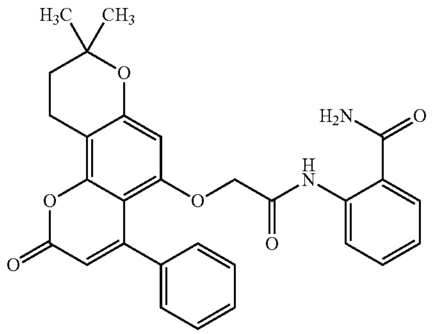 [SMILES: CC1(C)CCc2c(cc(OCC(=O)Nc3ccccc3C(N)=O)c3c(-c4ccccc4)cc(=O)oc23)O1]

or a pharmaceutically acceptable salt thereof.

In a further aspect, the present invention relates to a compound (formula I) that binds to a CLOCK protein and negatively modulate CLOCK:BMAL1 activity.

The present invention relates to a novel CLOCK-binding small molecule that affects the translocation of the CLOCK protein into nucleus through the modulation of the BMAL1 and CLOCK interaction and thus enhances circadian rhythm. CLOCK and BMAL1 are dynamically interacting. When formula I is present, it binds to CLOCK and reduces CLOCK and BMAL1 interaction. Upon binding of formula I to CLOCK, the translocation of the CLOCK into nucleus abolished. Thus, formula I enhances the amplitude of the circadian rhythm.

In one embodiment of the invention, the disclosed compound exhibits selectivity and high affinity for the CLOCK protein. Thus, the inhibition is potent.

In certain aspects, the compound binds to the hollow between the α2 helix of bHLH domain and HB strand of PAS-A domain of CLOCK. With the exception of CRYPTOCHORME other core clock components known as PERIOD, CLOCK and BMAL1 clock proteins contain PAS domains; yet, results confirm the specific binding of the compound to CLOCK.

Binding of the compound to CLOCK inhibits the interaction between the CLOCK and BMAL1, thereby disrupting an existing CLOCK:BMAL1 heterodimer complex. This inhibition results in a reduction in CLOCK:BMAL1 dimerization and, in turn, the translocation of CLOCK into the nucleus through the modulation of the BMAL1 and CLOCK interaction.

Moreover, it is found that the compound affects the amplitude of circadian rhythm with no period change by decreasing the amount of CLOCK in the nucleus without affecting the protein levels in negative arm (CRY-PER2) or BMAL1. According to the invention, the compound enhances circadian rhythm amplitude persistently.

As used herein, the term "inhibit", "inhibition" or "inhibiting" refers to the reduction or suppression of a given condition, symptom, or disorder, or disease, or a significant decrease in the baseline activity of a biological activity or process such as CLOCK:BMAL1 interaction.

The term "a therapeutically effective amount" of a compound of the present invention refers to a non-toxic and sufficient amount of the compound of the present invention that will elicit the biological or medical response of a subject, for example, reduction or inhibition of the protein: protein interaction, or ameliorate symptoms, alleviate conditions, slow or delay disease progression, or prevent a disease or disorder, etc.

All of the various embodiments of the present invention as disclosed herein relates to methods of treating and/or preventing various diseases and disorders as described herein. As stated herein the compound used in the method of this invention are capable of inhibiting the effects of ClOCK: BMAL1 heterodimer complex.

The invention further provides methods for the treatment or prevention of circadian rhythm related disorders and diseases. Non-limiting examples of circadian rhythm disorders include aging, sleep disorders, altered metabolism (metabolic syndromes), obesity, diabetes, mood disorders, cancer and cardiovascular diseases. Mood disorders including major depressive disorder, bipolar I disorder; sleep disorders including circadian rhythm sleep disorders such as shift work sleep disorder, jet lag syndrome, advanced sleep phase syndrome, non-24-hour sleep-wake syndrome, irregular sleep-wake rhythm and delayed sleep phase syndrome.

Moreover, the invention relates to a pharmaceutical composition comprising such compounds, uses and methods of use for such compounds in the treatment and/or prevention of disorders associated with the circadian rhythm. In other embodiment of the present invention, a pharmaceutical composition comprising the compound is useful in the treatment and/or prevention of circadian rhythm related diseases and disorders due the inhibition of CLOCK:BMAL1 interaction.

The present invention relates to pharmaceutical compositions comprising a pharmaceutical carrier and a therapeutically effective amount of a compound of formula I, or a pharmaceutically acceptable salt thereof.

The present invention also relates to pharmaceutical compositions to treat and/or prevent a CLOCK-mediated disorder, such as different metabolic syndromes during in aging, mood disorders and diseases related to dampened the circadian rhythm. With age, not only the sleep-wake rhythm, secretion rhythm of hormones, such as melatonin involved in deep body temperature and sleep, are known to reduce a variety of physiological rhythms, biological clock is involved in sleep disorders associated with aging.

In one aspect, the disclosure relates to a method for the manufacture of a medicament for inhibiting CLOCK and BMAL1 interaction in a mammal comprising combining a therapeutically effective amount of a disclosed compound with a pharmaceutically acceptable carrier or diluent.

The present invention provides a method for identifying a compound for inhibiting the interaction between CLOCK and BMAL1. The method can be established using systems for pharmaceutical screening that are well known in the art.

In one aspect, the present invention provides a method for identifying a compound that inhibits the interaction between CLOCK and BMAL1, wherein the method comprises contacting a compound with CLOCK protein under conditions allowing for the interaction of the compound with CLOCK and/or BMAL1, and determining whether the compound inhibits the interaction between CLOCK and BMAL1 by using a system that uses a signal and/or a marker generated by the interaction between CLOCK and BMAL1 to detect presence or absence or change of the signal and/or the marker. The term "signal" as used herein refers to a substance that can be detected directly by itself based on the physical properties or chemical properties thereof. The term "marker" refers to a substance that can be detected indirectly when the physical properties or biological properties thereof are used as an indicator.

These examples are intended to representative of specific embodiments of the invention and are not intended as limiting the scope of the invention.

SPECIFIC EMBODIMENTS

In these embodiments, a structure-based design was applied to find small molecules that specifically bind to the circadian core CLOCK protein. After identifying candidate molecules by virtual screening, experimental studies lead to discover a compound (formula I) that specifically binds to CLOCK. It regulates the interaction between CLOCK and BMAL1 by interfering with the translocation of CLOCK into the nucleus both in vivo and in vitro. Further studies indicated that formula I enhances the amplitude of the circadian rhythm at the cellular level by stabilizing the negative arm of the transcriptional/translational feedback loop without affecting the period length.

EXAMPLES

Example 1 in Silico Search for Compounds that Interact with CLOCK

Molecular Dynamics of CLOCK

The initial structure of the CLOCK protein was obtained from the Protein Data Bank (PDB ID: 4F3L) (Huang et al., 2012). Molecular Dynamic (MD) simulations were carried out by NAMD (Phillips et al., 2005) software using CHARMM force field. First, the protein structure files (PSF) for MD simulations were prepared by VMD (Humphrey et al., 1996) after removing crystallographic water molecules and adding hydrogen atoms using AutoDockTools4 (Morris et al., 2009). Using the psfgen package, atom and residue names were replaced with the ones recognized by NAMD. Then, the structure was dissolved in a water-box and the system was ionized. In the first 10000 steps of minimization, the backbone was fixed. Further 10,000 steps of minimization were performed on all atoms with no pressure control. Subsequently, the system was brought to physiological temperature (310 K) by 10 K increments with 10 ps simulation for each increment in which alpha-carbons were restrained. The constraint scaling decreases from 1 to 0.25 kcal/(mol Å2) in 0.25 increments, with each increment being 5,000 steps. Further 90,000 steps with zero constraint scaling were performed as the final part of energy minimization before RMSD of protein was converged and stabilized. MD simulation for equilibrium was performed using the Langevin dynamics at 310 K with a damping coefficient of 5 ps-1, 1 atm constant pressure and the Langevin piston period and decay of 100 and 50 fs respectively. The bonded interactions, the van der Waals interaction with 12 Å cutoff, and the long-range electrostatic interactions with the particle-mesh Ewald (PME) were considered in the calculations of the forces acting on the system. At the end, the RMSD of the CLOCK backbone with respect to its initial structure showed that the equilibrium was reached after 3-4 ns. The final structure of the CLOCK after 10 ns of simulation was used as the receptor for docking step.

Docking Setup

After MD simulations, water molecules of the system were deleted and the PDBQT file of the receptor, CLOCK, was prepared using AutoDockTools4 (Morris et al., 2009). The library of commercially available small molecules (by Ambinter) was filtered according to “Lipinski’s Rule of Five” (Lipinski, 2000) considering a maximum limit of one violation. Finally, approximately 2 million small molecules were selected for docking. PDBQT files of ligands were prepared by means of an automated script in Python language. We used AutoDock Vina for estimating protein-ligand affinity and predicting the best binding conformations of the compounds. The search space was defined to include the whole CLOCK protein to perform blind docking. The exhaustiveness was set as the default. Ultimately, the compounds were ranked based on their binding affinities (kcal/mol). The protein-compound interactions of the top 500 hit compounds were visually examined by the Discovery Studio Visualizer. The threshold value for hydrogen bonding was set as 3.4 Å and the accessible surface area was created considering a radius of 1.4 Å for solvent molecules. In the process of selecting hit molecules, compounds with docking positions far from CLOCK:BMAL1 protein interfaces were eliminated. A final number of 100 compounds with affinities ranging from −7 to −10 kcal/mol was reached by considering features such as favorable shape complementarity and diversity in binding region and chemical properties. The top 100 compounds were then tested experimentally.

Example 3 Cell Cytotoxicity Test

The toxicity of the compounds was assessed by MTT-based assay using immortalized human osteosarcoma (U2OS) cells treated with different compounds at different concentrations. Cell viability was measured with MTT-based cell cytotoxicity test. U2OS cells were seeded on 96-well plate with $4\times10^3$ cell/well density. Two days later, the cells were treated with an appropriate amount of different small molecules. Control cells were treated with 0.5% vehicle (DMSO). After 48 hours, the media was replaced with a 20% solution of 5 mg/ml MTT in DMEM. After 4 hours of incubation, the media was discarded and a 1:1 solution of ethanol and DMSO was used to dissolve the formazan crystals. Cell viability was measured as stated in Sigma-Aldrich product information.

Compounds with a relative cell viability of less than 80% at 1.25 μM were eliminated. The final concentration of a non-toxic compounds for in vitro experiments was set to the maximum concentration at which it had at least 80% relative cell viability. Ultimately, 72 compounds were statistically identified as non-toxic and used for the next characterization step.

Example 4 Mammalian Two-Hybrid Assay

The procedure was carried out according to Checkmate-Promega’s protocol. Samples were examined in triplicate sets in a 96-well plate. HEK293T cells with the density of $4\times10^4$ cell/well were transfected with 50 ng of pG5-luc, 50 ng of pACT-mBmal1, 50 ng of pBind-hsClock plasmids and 0.5 ng of pRL-TK for normalization. Following the transfection, the cells were treated with different concentrations of small molecules. Control cells were treated with 0.5% vehicle (DMSO).

Ultimately, luminescence was measured using Dual-Luciferase Reporter Assay System (Promega) with Fluoroskan Ascent FL plate reader.

Example 5 Real-Time Monitoring of Circadian Rhythm

We used Bmal1::dluc U2-OS and Per1::dluc NIH 3T3, and continuously monitored the bioluminescence to record circadian rhythm. This experiment was performed in 96-well plates (triplicates) and 35-mm dishes (duplicates) in the secondary screen and detailed characterization steps respectively. Briefly, cells were seeded to reach confluency. A day after, the medium was replaced with DMEM containing 0.1 μM Dexamethasone to synchronize cells. Two hour later, 0.1 mM of Luciferin was freshly added to the recording medium (low glucose DMEM powder (with L-glutamine) supplemented with 10 mM HEPES, 0:35 mg/ml sodium bicarbonate, 3.5 mg/ml D-(+)-glucose powder, 5% FBS, 0.1 mM NEAA, 100 U/ml penicillin and 100 mg/ml streptomycin). Then, the medium was replaced with recording medium containing appropriate amount of each compound. Control cells were treated with 0.5% vehicle (DMSO). For a detailed characterization of CLK8, whenever required, and without any further medium change, small molecule treatment was postponed to two days after bioluminescence recording started. The 96-well plates were covered and bioluminescence was monitored by Synergy H1 Hybrid Multi-Mode Reader every 32 minutes. Similarly, we sealed the 35-mm plates with vacuum grease prior to mounting them on a LumiCycle luminometer (Actimetrics). Bioluminescence was recorded every 10 minutes for 4-6 days. Raw data (counts/sec) were plotted against time. The period and amplitude parameters were obtained using LumiCycle Analysis software (Actimetrics). First, the raw data was baseline fitted (n=1), and then the baseline-subtracted data was fitted to a sine wave (damped). The first day’s data was excluded from the analysis due to transient perturbations of luminescence after the medium change.

Example 6 Pull-Down Assay

HEK293T cells were transiently transfected with tag-free hsClock and mBmal1. After 48 hours of transfection, cells were harvested and whole cell lysate was prepared with ice-cold lysis buffer (50 mM Tris-HCl pH 7.4, 2 mM EDTA, 1 mM $MgCl_2$, 0.2% NP-40, 1 mM sodium orthovanadate, 1 mM sodium fluoride and protease inhibitor cocktail) followed by centrifugation at 7000×g at 4° C. for 10 minutes. Lysate was diluted with ice-cold 2× binding buffer (100 mM Tris-HCl pH 7.4, 300 mM NaCl, 0.2% NP-40, 2 mM sodium orthovanadate, 2 mM sodium fluoride, and protease inhibitor cocktail) 27. The lysate was divided into three fractions to be treated with either DMSO, or 20 μM of bitoinylated-CLK8 (bait) with or without 200 μM CLK8 (competitor). The lysate-compound samples were incubated and mixed continuously at 4° C. for 1 hour. After equilibrating NeutroAvidin Agarose resin (Thermo Scientific) with lysis buffer, the lysate-compound mixture and NeutroAvidin Agarose resin were incubated and mixed continuously at 4° C. overnight. The beads were washed four times with 1× binding buffer. To elute the bound proteins Laemmli buffer was added and samples were heated at 95° C. for 7 minutes. The pull-down precipitates were subjected to SDS-PAGE and transferred to a PVDF membrane (Millipore). Anti-CLOCK (Bethyl) and anti-BMAL1 (Santa Cruz Biotechnology) antibodies were used to detect CLOCK and BMAL1 proteins respectively. The LC-MS/MS examination of the pull-down precipitates was performed in Koc University's Proteomics Facility. Bitoinylated-CLK8 and CLK8 were synthesized by Enamine, Ukrine.

Example 7 Co-Immunoprecipitation

HEK 293T cells co-expressing wild type or F80A-K220A mutant FLAG-tagged Clock together with tag-free Bmal1 were lysed with ice-cold lysis buffer (50 mM Tris-HCl PH 7.7, 150 mM NaCl, 0.1% Triton X-100, 1 mM PMSF and protease inhibitor cocktail) and centrifuged at 15000×g at 4° C. for 20 minutes. DMSO and different concentrations of CLK8 were added to the whole cell lysate. The mixtures were incubated with anti-FLAG M2 affinity gel (Sigma-Aldrich) at 4° C. overnight with continuous mixing. After three wash steps, bound proteins were eluted with Laemmli buffer heated at 95° C. for 7 minutes. CLOCK and BMAL1 were detected by monoclonal anti-FLAG M2 antibody (Sigma-Aldrich) and anti-BMAL1 (Santa Cruz Biotechnology) respectively. The amount of co-precipitated BMAL1 was normalized with the amount of precipitated CLOCK.

Example 8 mRNA and Protein Analysis

Unsynchronized Bmal1::dluc U2OS cells were seeded on 6-well dishes. Confluent cells were treated with an appropriate amount of CLK8 for 48 hours. Control cells were treated with 0.5% vehicle (DMSO). After harvesting the cells, mRNAs were isolated (RNeasy, QIAGEN) and converted to cDNA (Thermo Scientific). Finally, cDNAs were subjected to SYBR Green-based RT-qPCR assay. PRLP0 was used as an internal control. The primers used in RT-qPCR are listed in Table 2. For western blot analysis RIPA buffer was used to prepare whole cell lysates. The amount of protein for each sample was normalized to the β-ACTIN amount detected by β-Actin antibody (Cell Signalling).

Example 9 Luciferase Degradation Assay

The procedure was similar to the one described in the previous study (Hirota et al., 2012). Briefly, HEK 293T cells were seeded in triplicates in opaque 96-well plates 24 hours prior to transfection. Cells were transiently transfected with 10 ng of pcDNA-dluc plasmid. After 24 hours, cells were treated with different concentrations of CLK8 or DMSO. A day later, luciferin and HEPES (pH 7.2) were added to the medium to the final concentrations of 0.4 mM and 10 mM respectively and incubated for one hour. Subsequently, protein synthesis was ceased by CHX treatment and the luminescence signal was recorded by Synergy H1 Hybrid Multi-Mode Reader for 20 hours. The results were first normalized and then fitted to one-phase decay to calculate the half-life of Luciferase protein.

Example 10 Transactivation Assay

HEK 293T cells with the density of $4\times10^4$ cell/well were transfected with 50 ng of mPer1-luc, 50 ng of Sport6-Bmal1 and 125 ng of Sport6-Clock (wild type) or 125 ng of Sport6-Clock (F80A-K220A) plasmids and 0.5 ng of pRL-TK for normalization. The same experiment was also performed using Flag-tagged constructs of CLOCK instead. Dual-Luciferase Reporter Assay System (Promega) was used to measure the luminescence by Fluoroskan Ascent FL plate reader.

Example 11 Site-Directed Mutagenesis

Site-directed mutagenesis of Sport6-Clock and pCMV-Flag-Clock was performed using platinum Pfx DNA polymerase (Invitrogen) as described in the product's manual. The primer sets are listed in Table 2.

Example 12 Cytosol-Nuclear Fractionation

U2 OS cells treated with 20 μM CLK8 and 0.5% DMSO were used for fractionation analysis. The $4\times10^5$ was suspended in 500 ul cytosolic lysis buffer (10 mM HEPES pH 7,9, 10 mM KCl, 0.1 mM EDTA, 0.05% NP40 with protease inhibitors) and incubated on ice for 10 minutes. The lysate was centrifuged for 3 minutes at 3000 rpm at 4° C. The resulting supernatant was centrifuged one more time and supernatant collected as cytosolic fraction. On the other hand, the resulting pellet from lysate centrifugation was suspended in nuclear lysis buffer (20 mM HEPES pH 7.9, 0.4 M NaCl, 1 mM EDTA, 10% glycerol with protease inhibitors) and sonicated 2 times 10 seconds with 60% power. After centrifuge at 15 000 g for 5 minutes at 4° C., supernatant was collected as nuclear fraction. Collected

TABLE 2

Primers for the site-directed mutagenesis of CLOCK. Bold indicates the mutated codon.

| Gene | Forward Sequence | Reverse Sequence |
|---|---|---|
| F80A-hsClock | CAGAAAAGCATTGAT**GCT**TTACGAAAAC ATAAAGAAATCACTGCACA (SEQ ID NO: 3) | CTGTGCAGTGATTTCTTTATGTTTTCGTA AAGCATCAATGCTTTTCTG (SEQ ID NO: 4) |
| K220Ahs Clock | GTAAAATTTATAGGAAATTTC**GCA**TCTTT AAACAGTGTATCC (SEQ ID NO: 5) | GGATACACTGTTTAAAGATGCGAAATTT CCTATAAATTTTAC (SEQ ID NO: 6) |

fractions were used for Western Blot analysis. Fractionation efficiency was checked with Western Blot by using tubulin (Sigma T9026) as cytosolic marker and Histone-H3 (abcam ab1791) as nuclear marker.

Example 13 Lentivirus Production and Transduction

HEK 293T cells at 75-85% confluency were transfected with 10 ng of pLV6-Bmal-luc plasmid, 9 ng of pCMV-AR8.2dvpr packaging vector and 1 ng of pCMV-VSVG envelope vector for 16 h. Next day, the medium was replaced with fresh growth medium. As lentiviral particles were harvested at 72-hour and 96-hour post-transfection. Clock-deficient and wild type MDA MB231 cells were transduced with Bmal1-luc lentiviral particles for 16 h. Medium was replaced fresh growth medium and transduction was repeated one more time. At 72-hour post-transduction, the circadian rhythms of cells monitored using Lumicycle.

Example 14 In Vivo Studies in Mouse Liver

Male C57BL/6J mice, 8 weeks of age, weighing 18-24 g were treated with two different single doses of CLK8 (25 mg/kg n=5 per each dose) intraperitoneally. Control mice (n=3) were only treated with vehicle (DMSO:Cremophor EL: 0.9% NaCl; 2.5:15:82.5, v/v, i.p.). Water and food were provided ad libitum throughout the experiments. Six hours after injection, mice were sacrificed by cervical dislocation. Liver tissues were removed, frozen in liquid nitrogen and stored at −80° C. until further processing.

Example 15 Quantification of Western Blot

All Western blots were obtained from Bio-Rad ChemiDoc Imaging System and the amount of each protein was quantified using Image Lab Software applying volume tools.

Example 16 Statistical Analysis

GraphPad Prism5 was used to assess statistical significance by two-tailed student's t-test. Biological replica were at least n=3 for all of the experiments. [*p-value<0.05,  p-value<0.01, * p-value<0.001.]

Results

The Effect of Hit Compounds on CLOCK:BMAL1 Interaction and Circadian Rhythm

Although the mammalian two-hybrid system (MTHS) is not a quantitative assay that is used to measure the degree of interaction between two proteins, we initially used MTHS to identify the compounds that significantly alter the interaction between CLOCK and BMAL1. Twenty four compounds significantly altered the CLOCK:BMAL1 interaction without changing the protein level (data is not shown), suggesting that they might modulate the positive feedback loop at the molecular level.

We then assessed the effect of these compounds on the circadian rhythm of U2-OS cells stably expressing Bmal1::dluc. The molecules had different effects on the circadian rhythm and were classified accordingly; amplitude-enhancers (9 compounds), period lengtheners (2 compounds), and amplitude-reducers (2 compounds). Subsequent to a dose response validation, only four compounds passed the secondary screening step successfully. To assess the specificity of these four compounds on different genetic background for the circadian rhythm, NIH 3T3 cells stably expressing Per1::dluc were subjected to these four compounds. Two compounds (one of them is CLK8) displayed the same phenotypic changes in both cell lines, suggesting that the core clock mechanism had been affected. The amplitude-enhancing compound, CLK8, was selected for further characterization. None of the amplitude-enhancing small molecules identified so far has affected the positive or negative TTFL of the circadian clock directly.

Before following the experimental procedure further, to assure that CLK8 did not interfere with the luminescence signal itself we examined the degradation rates of LUC in HEK293T cells transfected with pcDNA-Luc and treated with CLK8. The half-life of LUC was unchanged in cells treated with CLK8 confirming luminescence signal as an independent and consistent measuring tool. Thus, the compound likely modulates CLOCK:BMAL1 activity.

The Effect of CLK8 on Circadian Rhythm

Figure 1B:
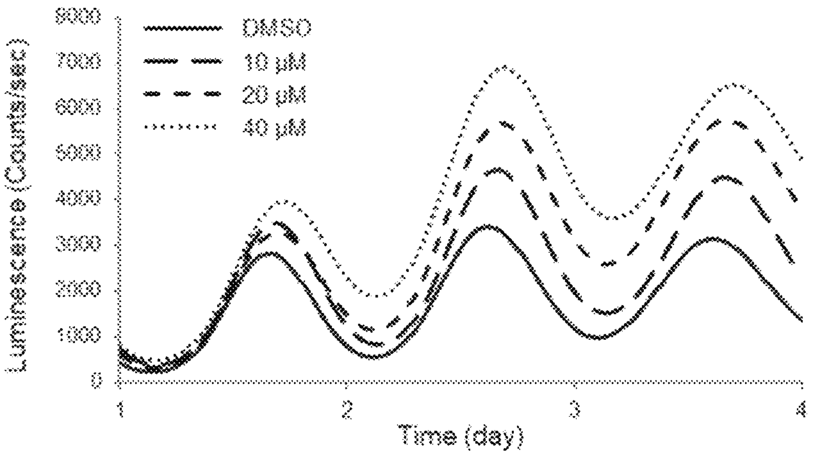
FIGS. 1B-1D show a dose-dependent cytotoxicity of CLK8 in U2OS cell line. All of the measurements were normalized to 0.5% DMSO control. (data are mean±s.e.m.; n=3 independent experiments.
Figure 1C:
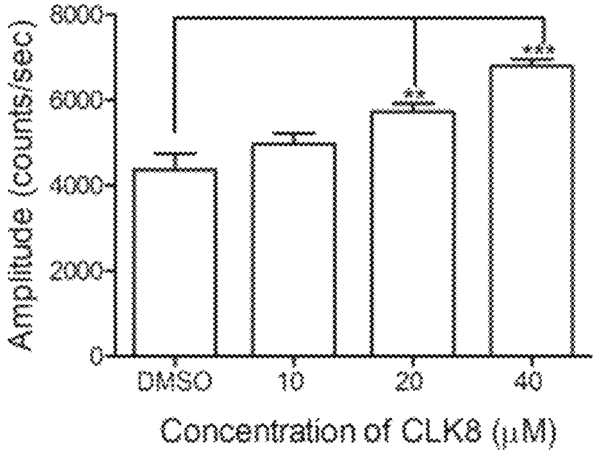
Figure 1D:
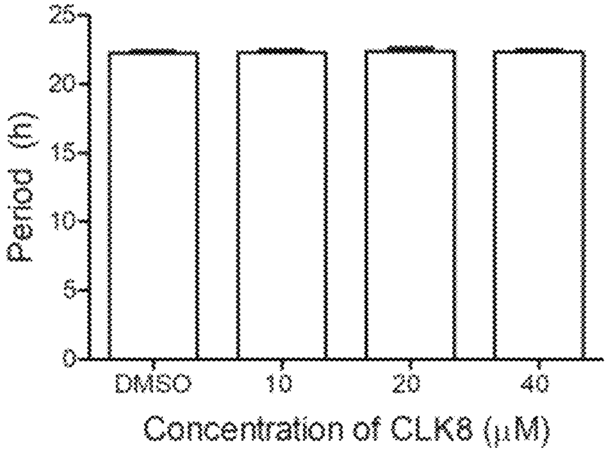
Figure 1E:
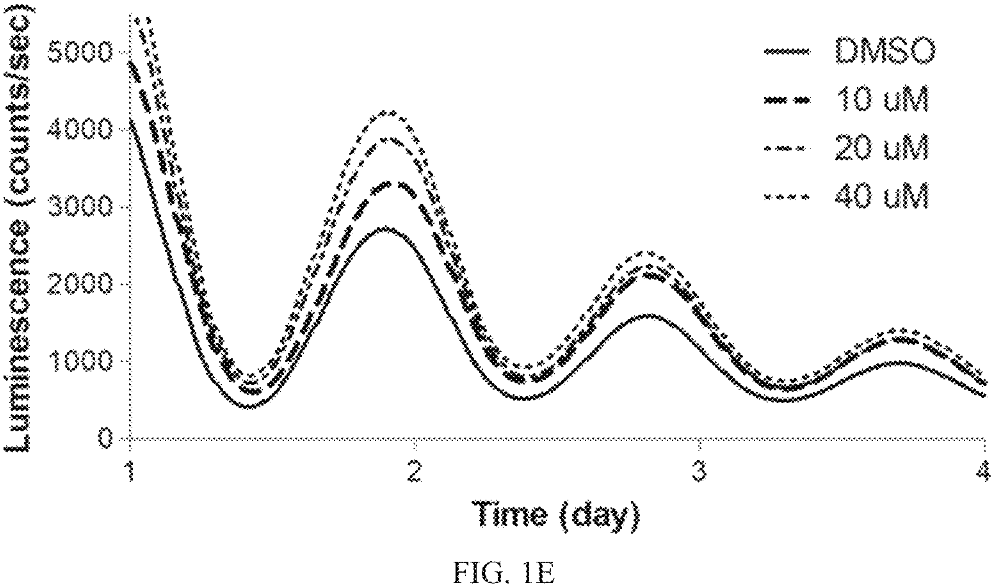
FIGS. 1E-1J show continuous monitoring of luminescence rhythms of Bmal1::dluc U2OS and Per1::dluc NIH 3T3 cells to determine dose-dependent effect of CLK8 on circadian rhythm. Amplitude and period parameters are shown in right panel.
Figure 1F:
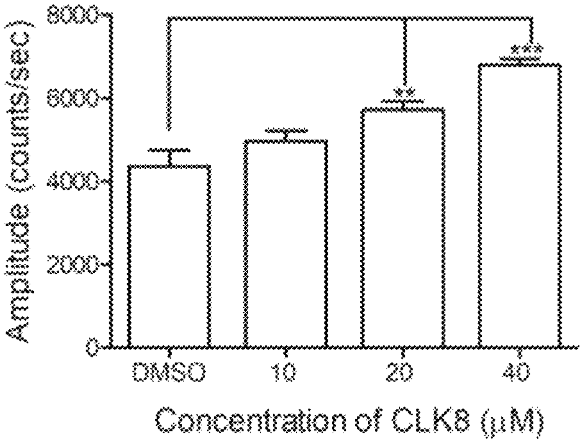
Figure 1G:
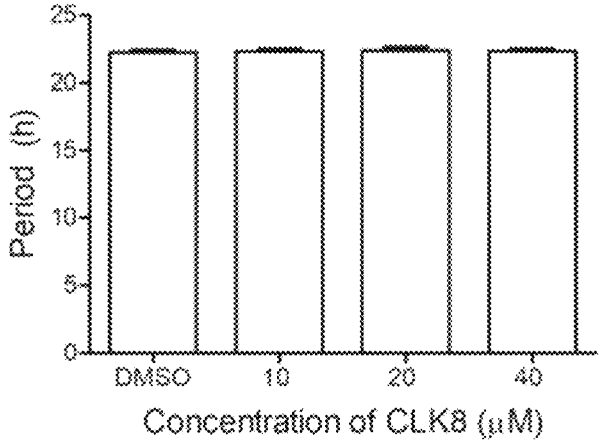
Figure 1H:
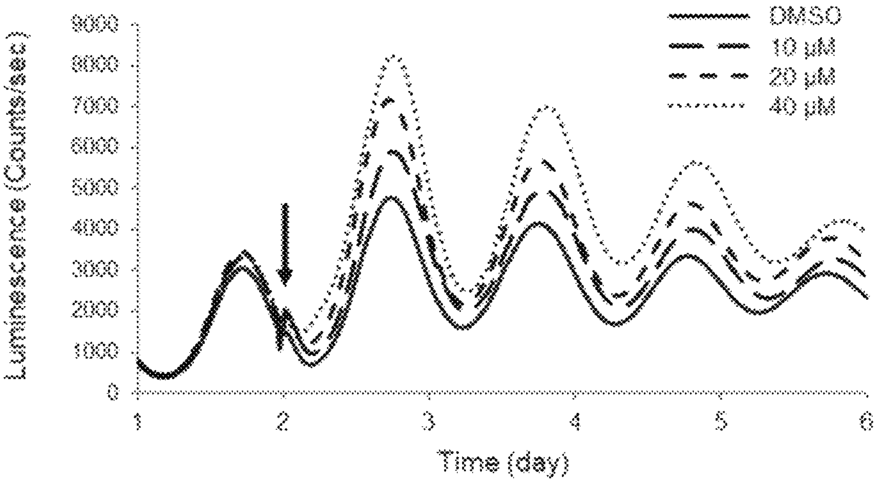
Figure 1I:
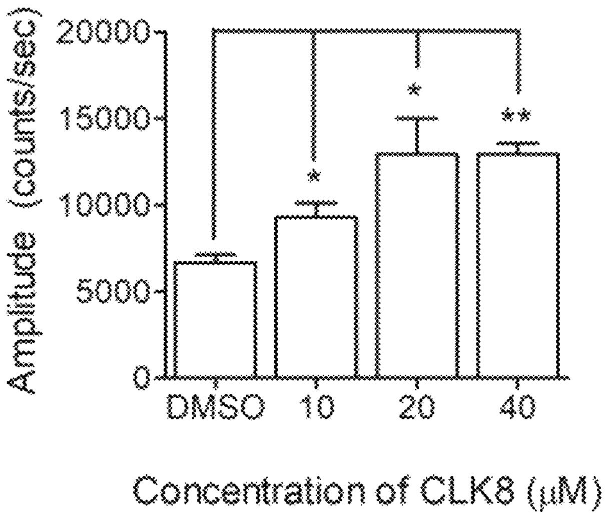
Figure 1J:
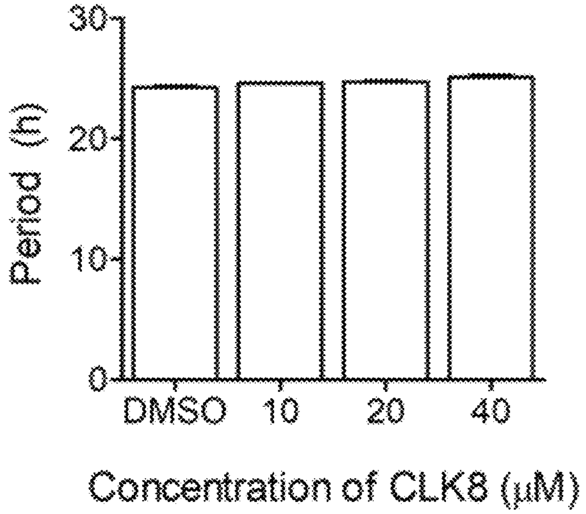
Figure 1K:
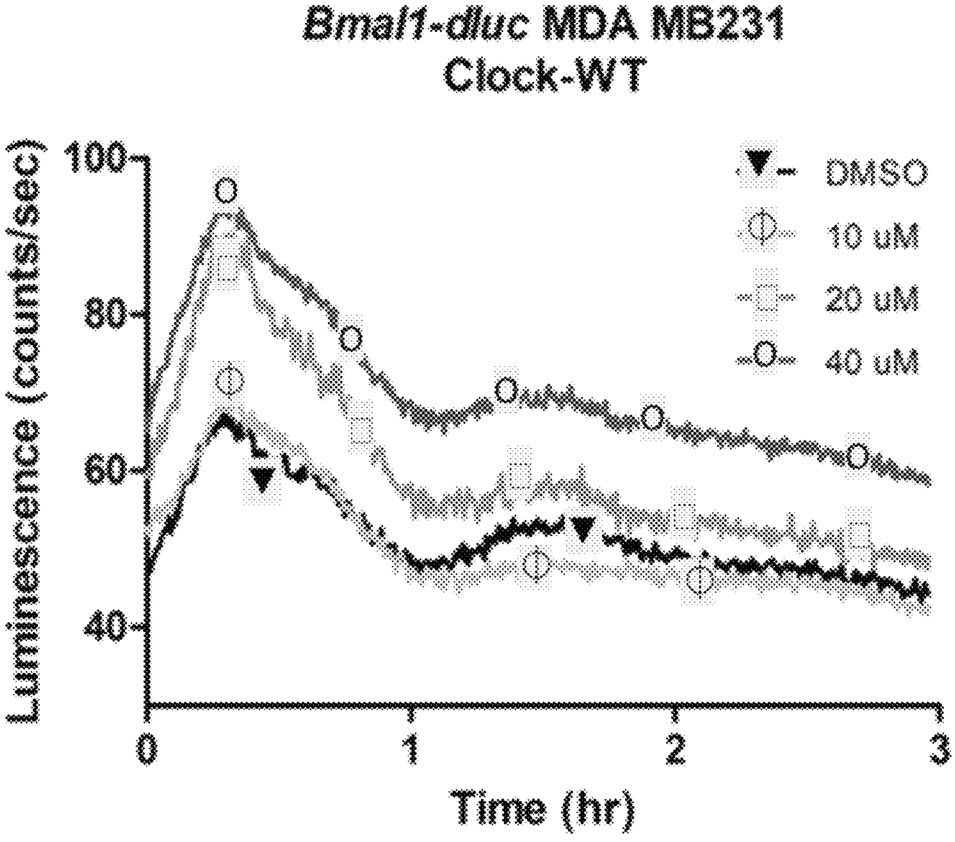
FIGS. 1K-1M show Bmal1::dluc U2OScells were synchronized at time 0. Two days later (black arrow), cells were treated with 10, 20, and 40 μM of CLK8. Cells treated with 0.5% DMSO were used as a control (luminescence profiles are the means of 3 independent experiments). Amplitude and period parameters (shown in right panel) were obtained by fitting first-order polynomial baseline-subtracted data with sin (damped). The first day was not included in analysis. (data are mean #s.e.m.; n=3 independent experiments). [* p-value<0.05;  p-value<0.01; * p-value<0.001]. (F) MDA MB231 wild type and FIGS. 1N-1P show clock knock-out MDA MB231 cells were transduced with Bmal1::dluc lentiviral particles. At 72 hour posttransduction, the luminescence rhythms of the cells were monitored continuously to determine dose dependent effect of CLK8 on circadian rhythm. Amplitude and period parameters (shown in bottom panel) were obtained by fitting first-order polynomial baseline-subtracted data with sin (damped). (Luminescence profiles are means of 3 independent experiments. data are mean±s.e.m.; n=3 independent experiments.). [* p-value<0.05]
Figure 1L:
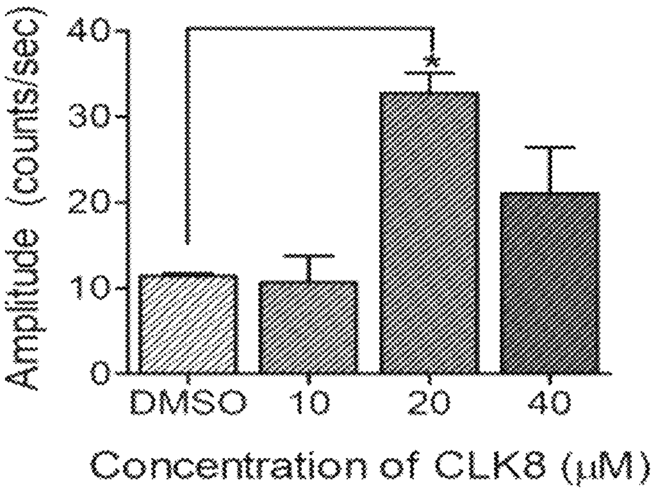
Figure 1M:
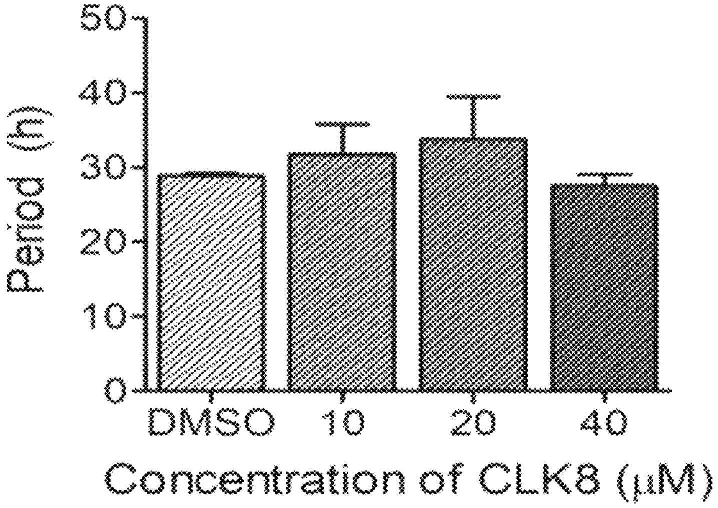
Figure 1N:
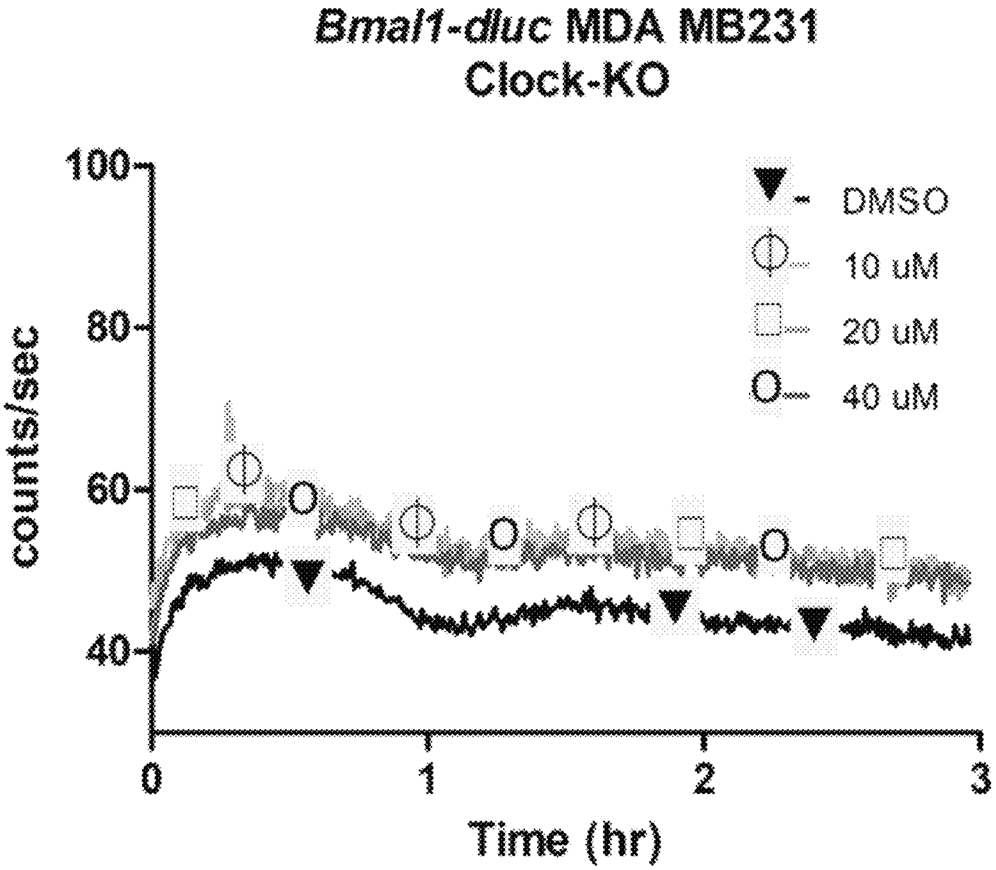
Figure 1O:
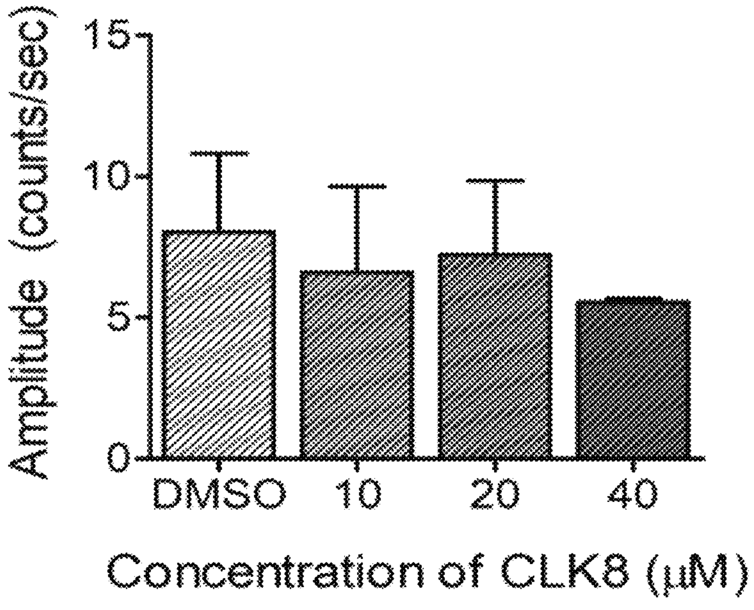
Figure 1P:
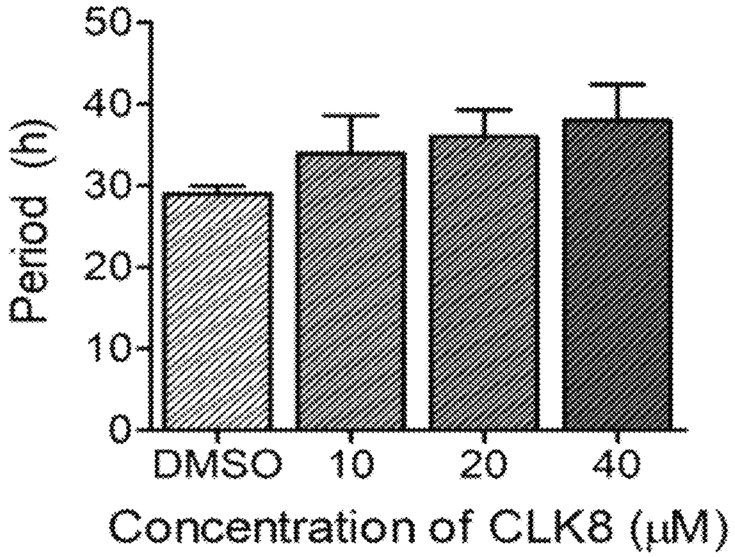

The maximum concentration of CLK8 used for in vitro experiments with cell viability higher than 80% was 40 UM and was not toxic to the U2OS cell line (FIG. 1A). Investigations into the effect of CLK8 on the circadian rhythm revealed that CLK8 enhances the amplitude of human U2OS cells stably expressing the Bmal1 promoter-driven luciferase reporter and performed kinetic bioluminescence assays to assess clock function (U2OS-Bmal1::dLuc) and mouse NIH 3T3 cells stably expressing the Per1 promoter-driven luciferase reporter (NIH 3T3-Per1::dLuc) in a dose dependent manner and no period changes were observed in both cell lines (FIGS. 1B-1G). We subsequently decided to monitor the reporter rhythm before and after small molecule treatment to better understand the effects of this compound. U2OS-Bmal1::dLuc cells were synchronized and the reporter rhythms were recorded for two days (FIGS. 1H-1J). Then, different doses of CLK8 were added to cells without replacing the media to prevent any phase resetting (31). Bioluminescence rhythms were recorded for four more days. The luminescence profiles of all the samples were the same until treatment with the small molecule. Compared to the DMSO control, CLK8 advanced the phase of the first trough right after treatment. The CLK8 was able to enhance the amplitude by more than 50% at 10 μM (FIGS. 1H-1J). We analyzed the effect of CLK8 on the Bmal1::dluc knock-in reporter in Clock-deficient and wild type MDA MB231 cells. CLK8 was able to enhance amplitude in wild type MDA MB231 cells (FIGS. 1K-1M) while CLK8-mediated increase in Bmal1-luc intensity was abolished in the Clock knockout cells at different concentrations of CLK8 (FIGS. 1N-1P). These results suggested that the molecule specifically binds CLOCK and results in amplitude enhancement.

Specific Binding of CLK8 to CLOCK

Figure 2A:
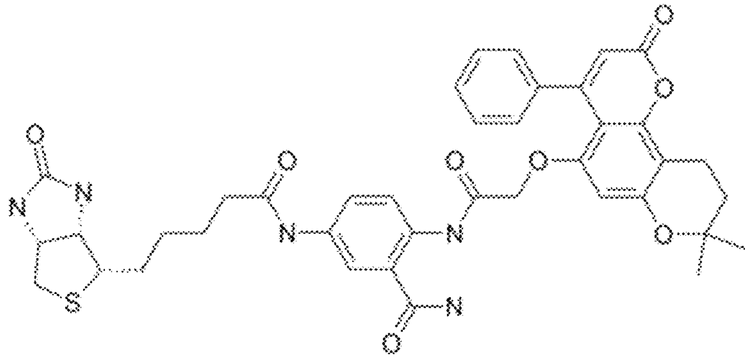
FIGS. 2A-2C are an illustration of specific binding of formula I to CLOCK.

Once CLK8 was identified as a promising molecule, its physical binding to CLOCK was assessed by pull-down assay using biotinylated CLK8 as bait. The biotinylated CLK8 was synthesized by Enamine, a chemical supplier in Ukraine (FIG. 2A).

Figure 2B:
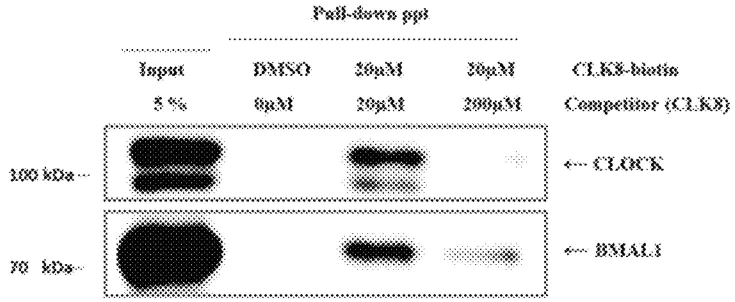
Figure 2C:
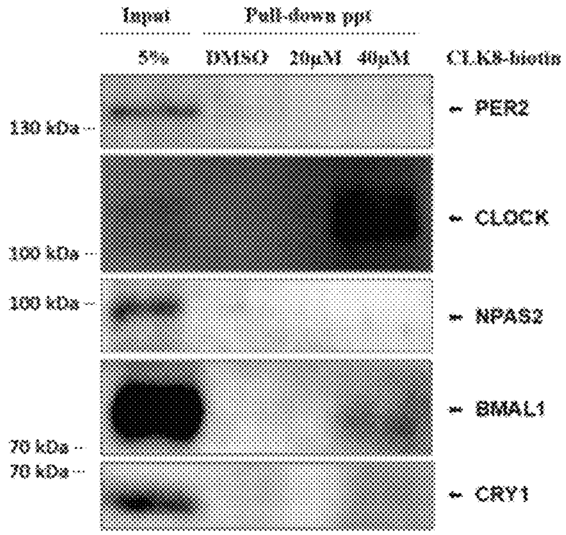

Whole cell lysate of HEK293T cells overexpressing CLOCK and BMAL1 were incubated with biotinylated CLK8 in the absence and presence of the competitor (CLK8). CLOCK was precipitated with biotinylated CLK8 but not in the presences of the free CLK8 (unbiotinylated CLK8) (FIG. 2B). The results showed that CLK8 specifically binds to CLOCK. Moreover, to eliminate any artifact of an overexpressed system, whole cell lysate of U2OScells expressing endogenous levels of CLOCK (and BMAL1) were used in a pull-down assay. The difference in the amount of CLOCK between the input and the sample precipitated with biotinylated CLK8 revealed that CLK8 has high affinity for CLOCK (FIG. 2C). Except BMAL1, which was always co-precipitated together with CLOCK (although in very low amounts), none of the other core clock components were detected as a target for CLK8 (FIG. 2C) including NPAS2, a homologue of the CLOCK gene. (human CLOCK nucleotide sequence; SEQ ID No: 1)

The next step was to check for off-targets of CLK8. Accordingly, LC tandem mass spectrometry was used to further analyze the precipitated proteins. Since the amount of precipitated endogenous CLOCK was insufficient to be detected in LC-MS/MS, whole cell lysate of HEK 293T cells overexpressing CLOCK and BMAL1 were used for LC-MS/MS. We determined proteins that potentially bind to CLK8 by utilizing a minimum threshold for peptide spectrum matches and coverage equal to those of the main target, CLOCK. We also excluded proteins that have been detected in negative controls of the CRAPome database (32), assuming them as abundant sticky proteins. In the presence of a competitor, CLOCK was not detected in MS/MS, which explicitly showed the specificity of the binding. BMAL1 was detected in lower amounts when a competitor was present. The decrease in the amount of NAV2 in the presence of the competitor introduced it as a possible off-target of CLK8 (Table 1).

TABLE 1

Potential targets of CLK8.

| Protein | | Peptide spectrum matches Competitor (μM) 0 | 200 |
|---|---|---|---|
| CLOCK | Circadian locomoter output cycles protein kaput | 42 | — |
| BMAL1 | Aryl hydrocarbon receptor nuclear translocator-like protein 1 | 56 | 46 |
| NAV2 | Neuron navigator 2 | 263 | 188 |

Figure 3A:
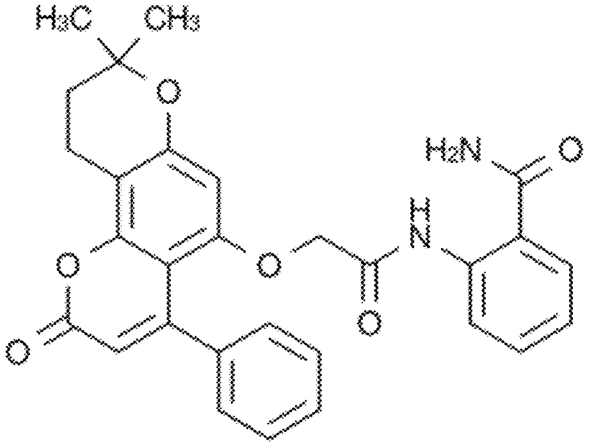
FIGS. 3A-3D are an illustration of the docking results of formula I.
Figure 3B:
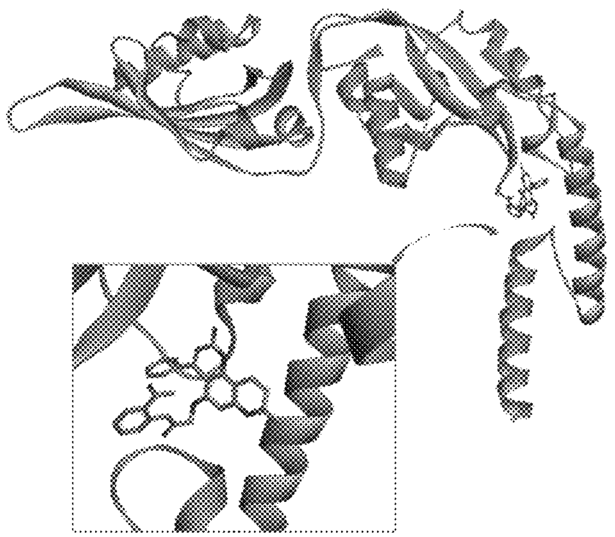
Figure 3C:
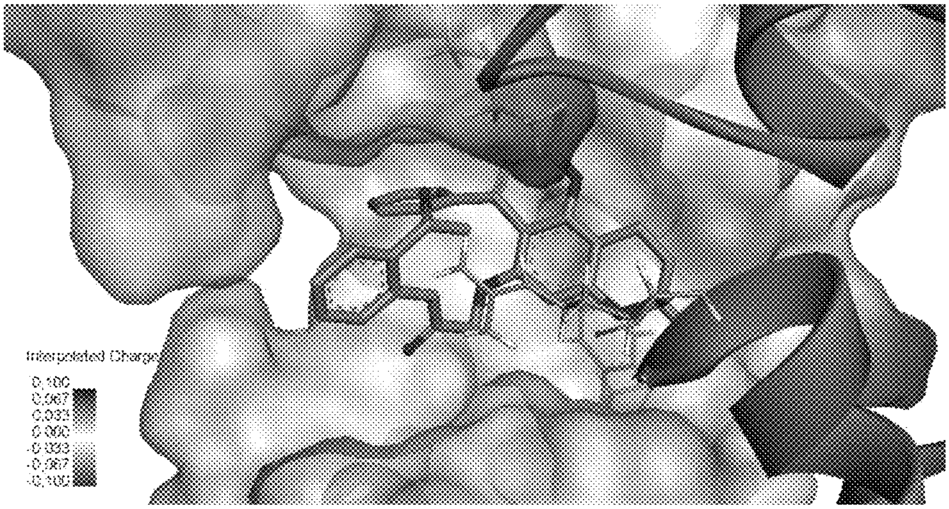
Figure 3D:
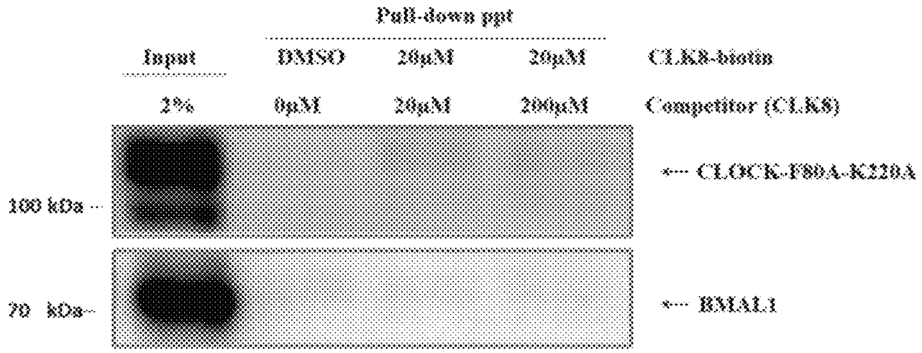

The docking results showed that FORMULA I (FIG. 3A) binds to the hollow created between the α2 helix of the bHLH domain and the HB strand of the PAS-A domain of CLOCK (FIG. 3B). Based on MD results of the CLOCK: BMAL1 heterodimer, this hollow is where Arg126 of BMAL1 enters and interacts with Phe80 of CLOCK, a conserved hydrophobic core residue on the α2 helix of the bHLH domain (FIGS. 3B-3C). Phe80, according to docking results, is also involved in the interaction between CLOCK and CLK8. Lys220 is another residue that plays an important role in the interaction of CLOCK and FORMULA I (also referred as CLK8) by offering a cation-pi interaction. To confirm the binding site, we replaced Phe80 and Lys220 of CLOCK with Ala by site-directed mutagenesis using appropriate primers. After generating the double mutant (CLOCK-F80A-K220A) we first determined the effect of the mutations on the functions of CLOCK by transactivation assay. To evaluate the functional consequences of these mutations on clock function, we monitored the activity of Per1::luciferase using CLOCK:BMAL1 and Clock-F80A-K220A/Bmal1 in HEK 293T cells. Analysis of the result showed both wild type and mutant clock had same degree of the activation on Per1::luciferase reporter along with BMAL1. Consequently, we used HEK 293T cells overexpressing CLOCK-F80A-K220A and BMAL1 to verify the predicted binding site of CLK8. We performed a pull-down assay using biotinylated CLK8 in the absence and presence of the competitor (CLK8). The results clearly indicated that mutant CLOCK did not precipitate with biotinylated CLK8 to the same extent as wild type CLOCK (FIG. 3D). Besides, the minute amount of precipitated mutant CLOCK did not disappear in the presence of the competitor (CLK8) suggesting the binding of CLK8 to the computationally predicted region (FIG. 3B). Notably, BMAL1 didn't appear in blot as in the case of the pull down experiment with the wild type clock (FIG. 3D) suggesting that BMAL1 comes with wild type CLOCK rather than non-specific binding to the molecule.

Investigation of the Interaction Between CLOCK and BMAL1 in the Presence of CLK8

Figure 4A:
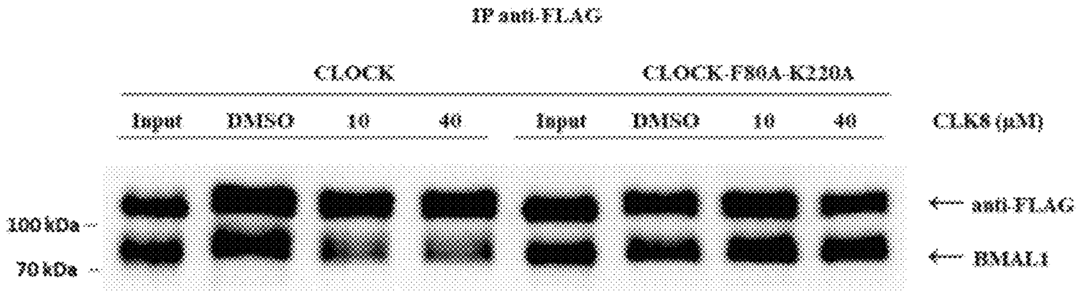
FIGS. 4A-4E are an illustration of reduction of CLOCK and BMAL1 interaction and nuclear localization of CLOCK by FORMULA I.
Figure 4B:
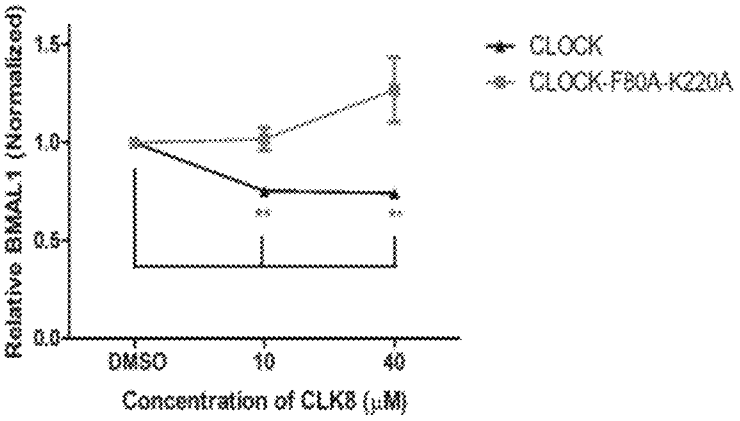

Mammalian two-hybrid results implied that CLK8 reduces the interaction between CLOCK and BMAL1. To test the effect of this molecule on the interaction between them, a co-immunoprecipitation assay was used. HEK 293T cells were transfected with plasmids encoding Flag-tagged CLOCK and BMAL1. An Anti-FLAG resin was used to precipitate FLAG-CLOCK at 10 μM and 40 μM of CLK8. While FLAG-CLOCK was precipitated to the same extent in all samples, the amount of BMAL1 reduced as the concentration of CLK8 increased (FIGS. 4A-4B). The results suggested that the interaction between CLOCK and BMAL1 decreases as the concentration of CLK8 increases (FIGS. 4A-4B). If this was true, we would expect the interaction between CLOCK F80A-K220A and BMAL1 to remain unaffected in the presence of CLK8. We then repeated pulldown experiment side by side using both mutant and wild type CLOCK. Results showed the BMAL1 and CLOCK interaction was reduced in the presence CLK8 while the interaction between CLOCK-F80A-K220A and BMAL1 was not affected even at 40 μM CLK8 (FIGS. 4A-4B). This data suggests that CLK8 interferes with the CLOCK and BMAL1 interaction.

The Effect of CLK8 on Subcellular Localization of CLOCK

Figure 4C:
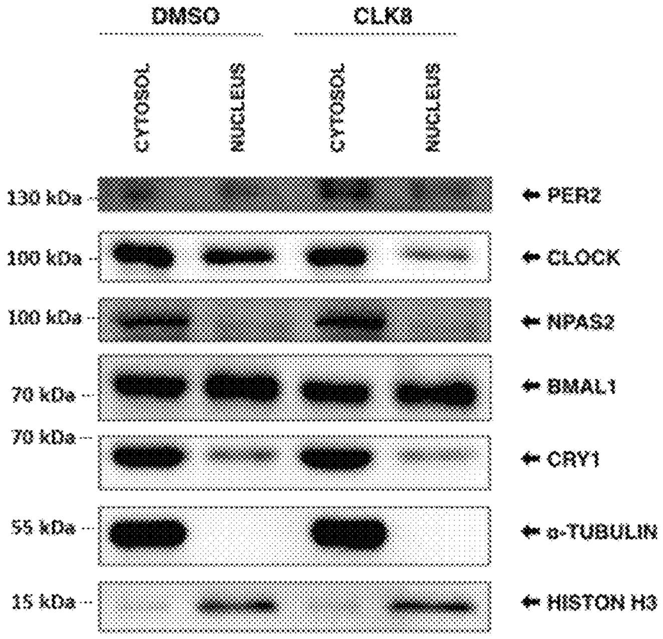
Figure 4D:
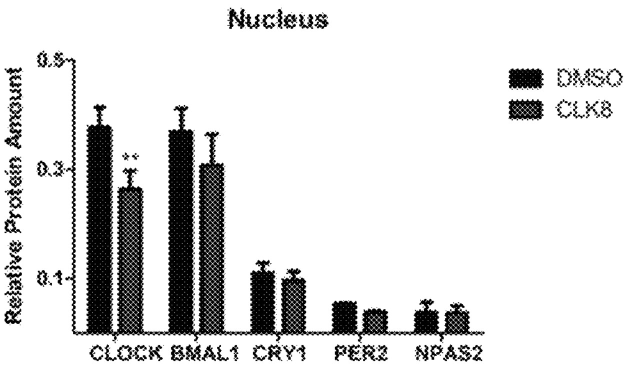
Figure 4E:
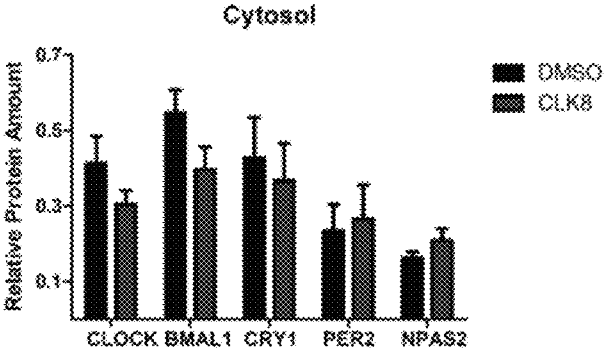
Figure 5A:
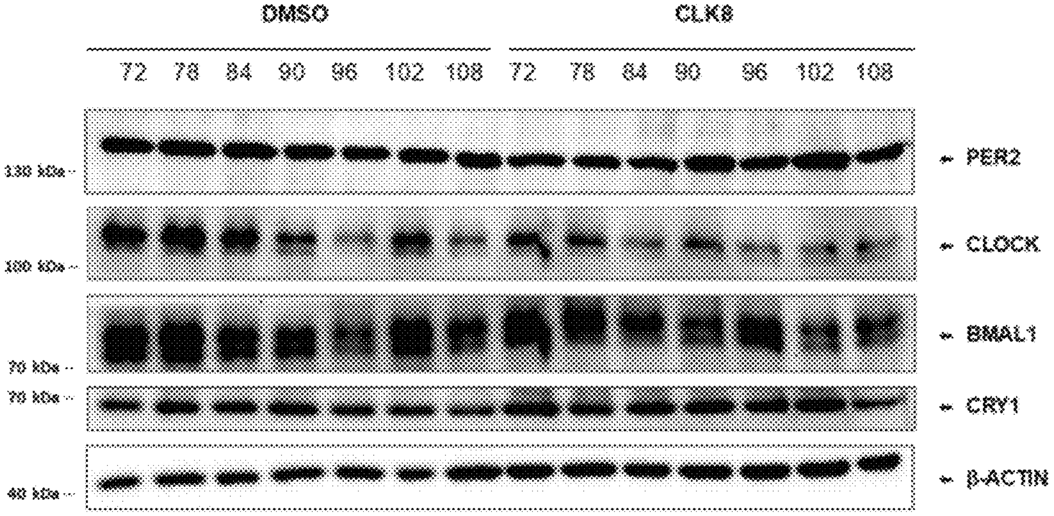
FIGS. 5A-5K are an illustration of FORMULA I altered CLOCK protein level in time dependent manner. Confluent U2OS cells were synchronized by 2-hours treatment with dexamethasone (0.1 μM) and medium replaced with fresh medium containing CLK8 or DMSO. Cells were harvested at indicated time points.
Figure 5B:
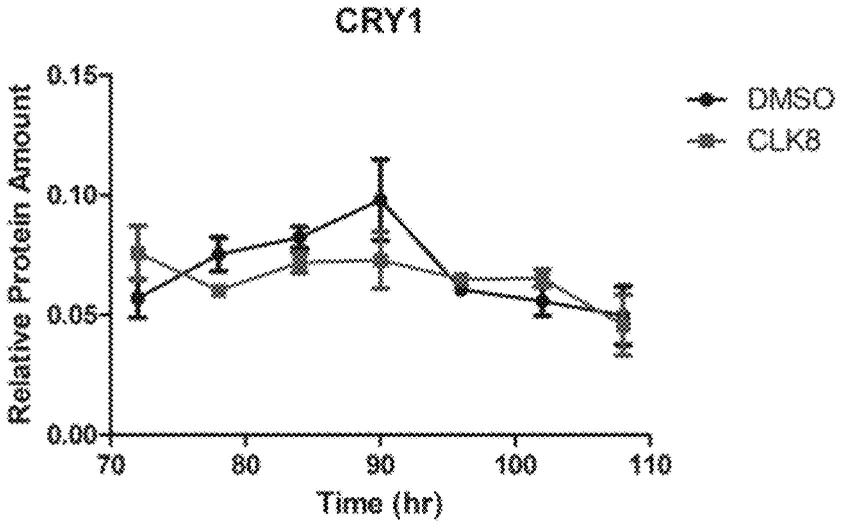
Figure 5C:
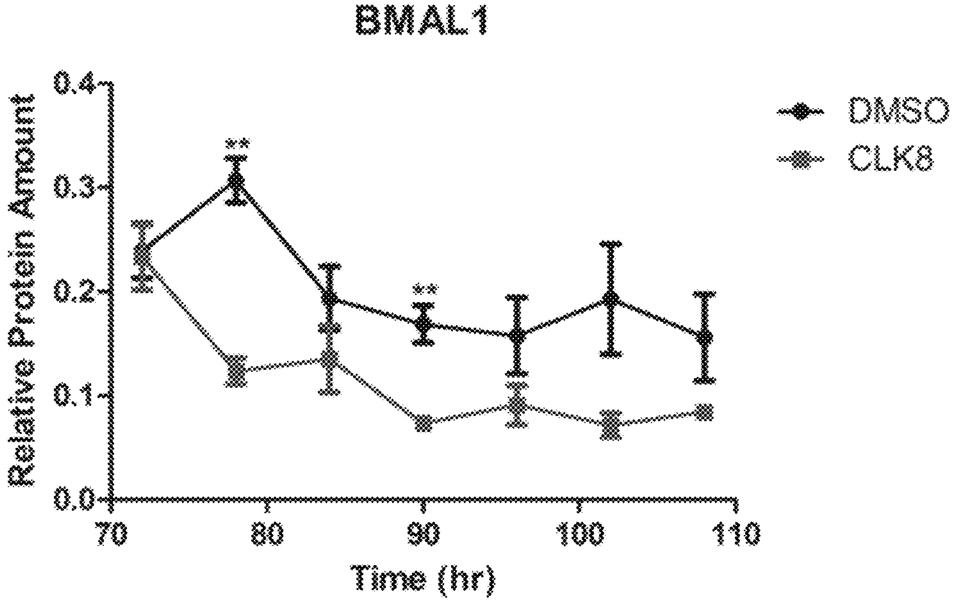
Figure 5D:
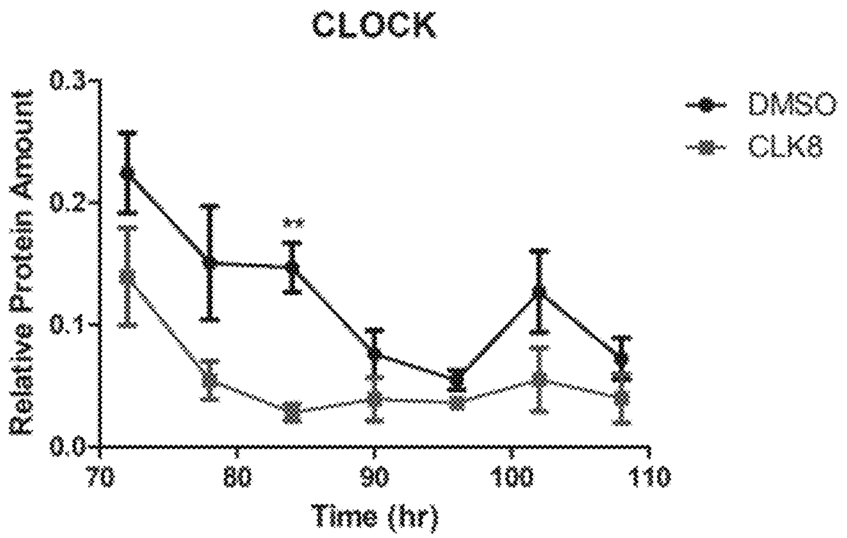
Figure 5E:
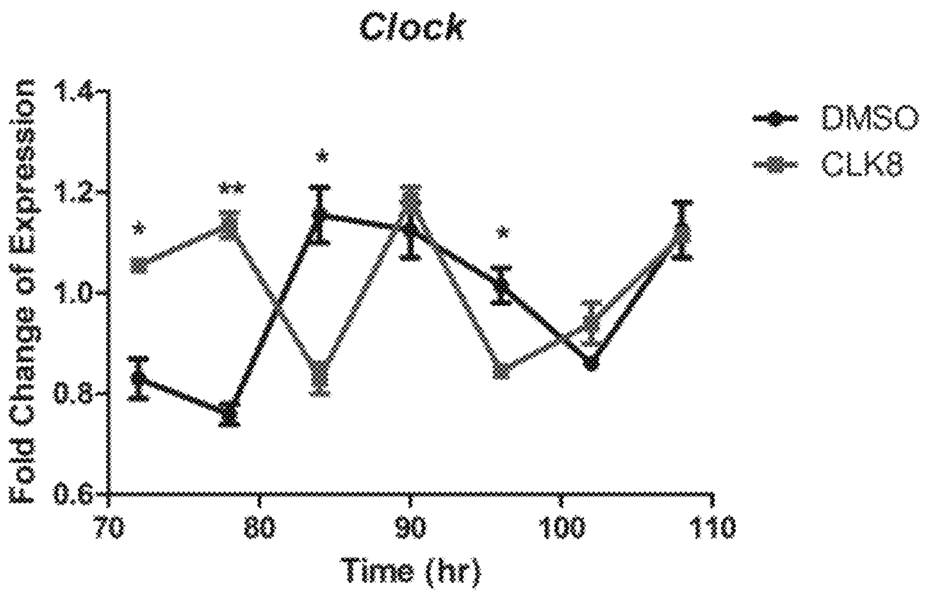
Figure 5F:
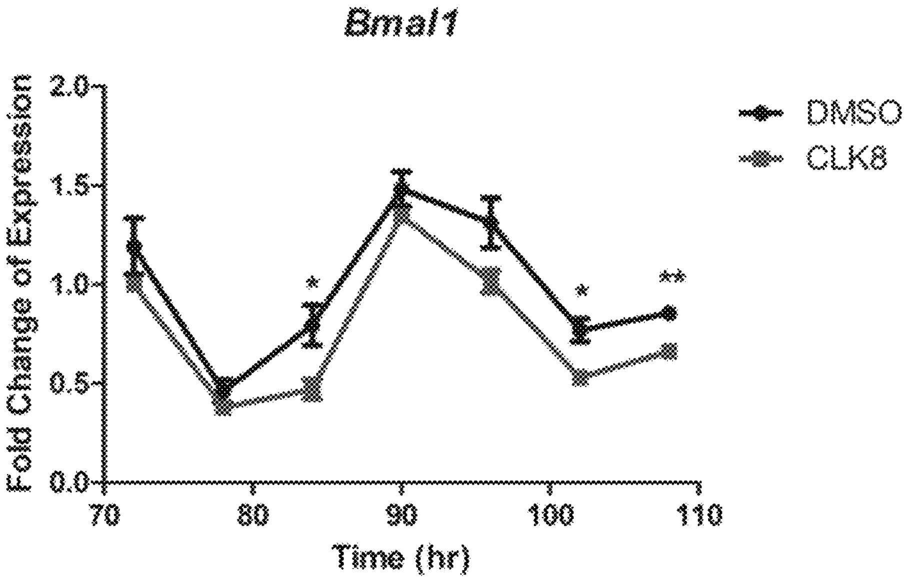
Figure 5G:
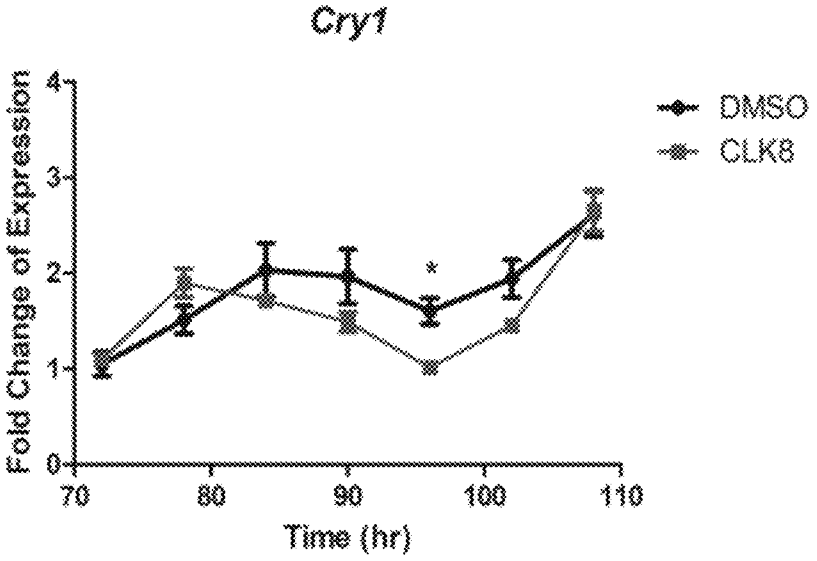
Figure 5H:
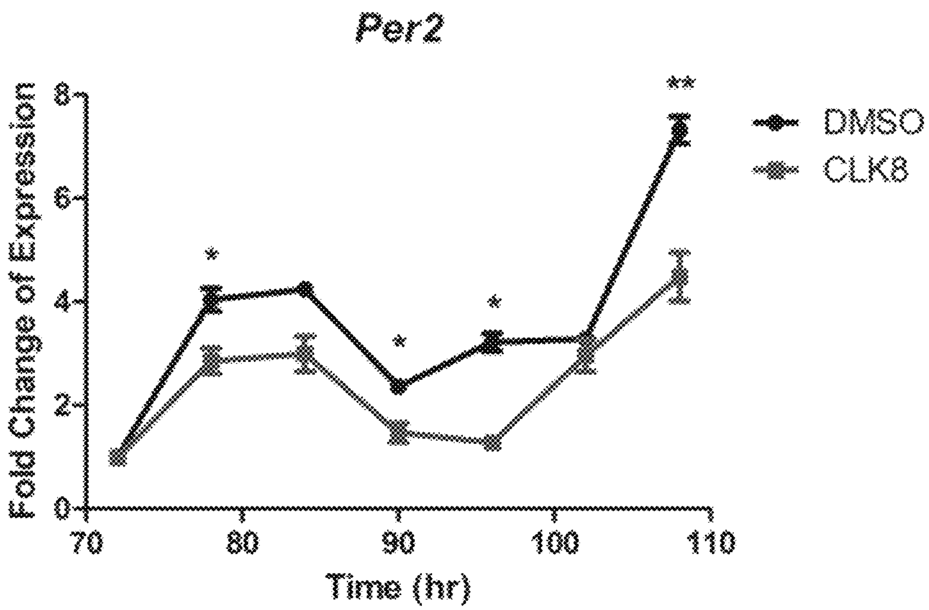
Figure 5I:
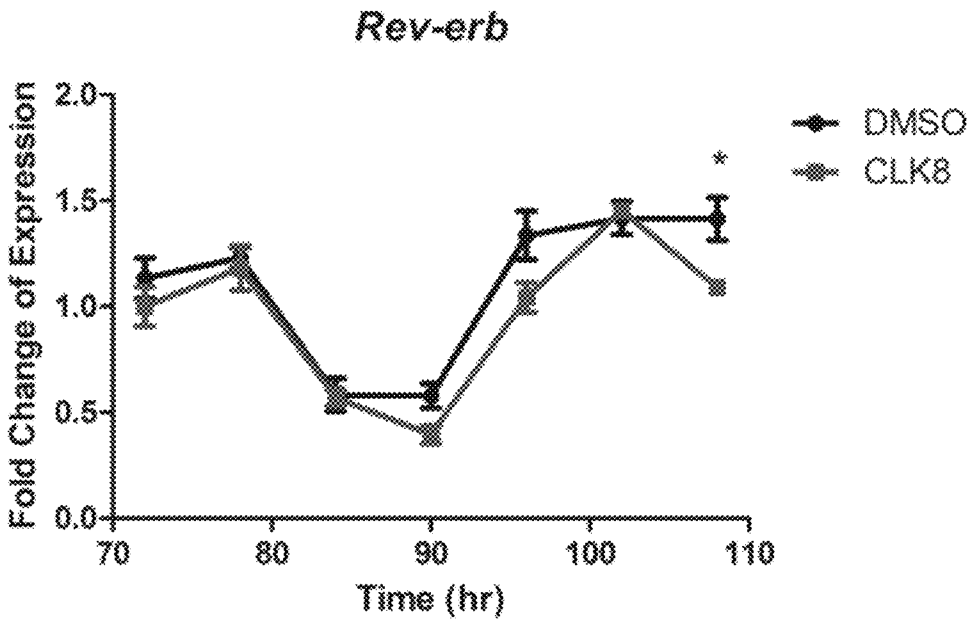
Figure 5J:
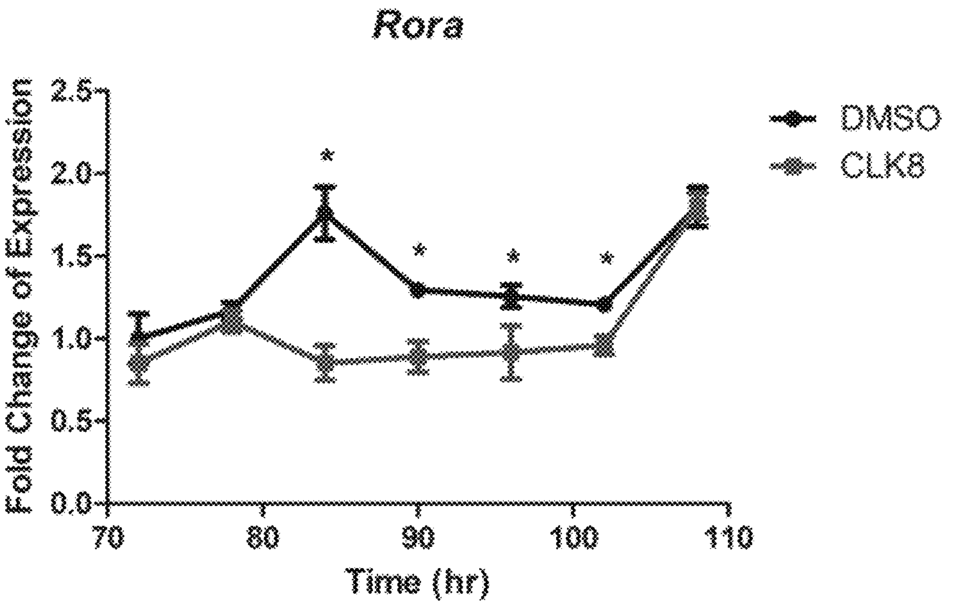
Figure 5K:
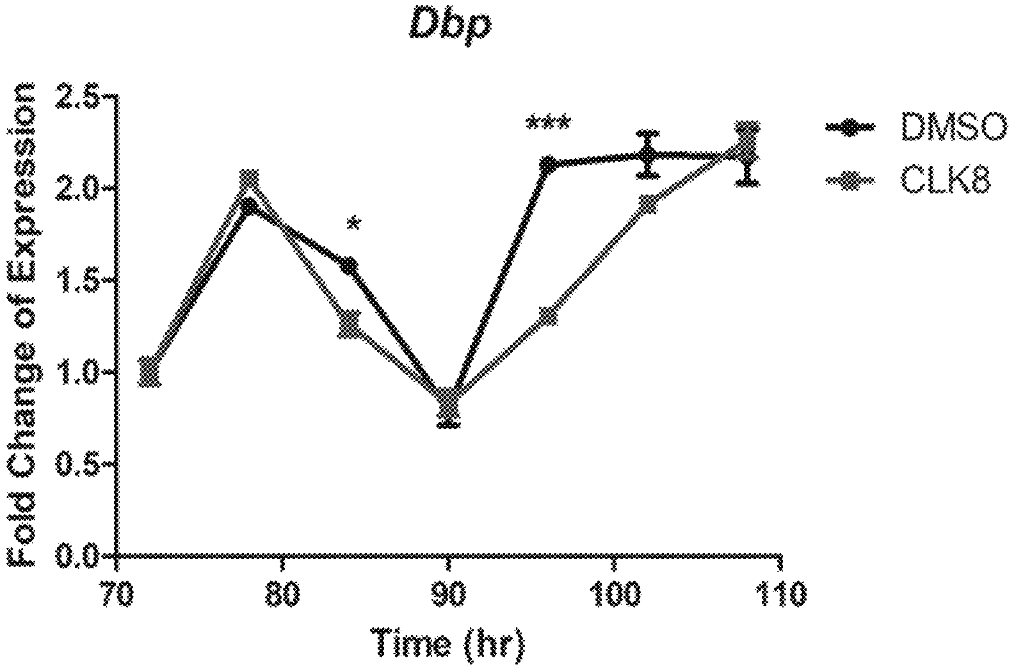

The localization and degradation of CLOCK is regulated by its direct interaction with BMAL1 (Kondratov et al., 2003). We hypothesized the inability of CLOCK binding to BMAL1 in the presence of the CLK8 molecule might alter subcellular localization of the CLOCK protein (SEQ ID NO: 2). To test that U2OS cells treated with 20 μM of CLK8 and cells were fractionated by isolating cytosolic and nuclear proteins. Proteins, specifically localized in the nucleus (Histone-H3) and cytoplasm (Tubulin), were used as controls to evaluate the purity of the fractions (FIGS. 4C-4E). Results indicated that the translocation of the CLOCK into the nucleus was affected the by the presence of CLK8 when compared to the control samples. The level of PER2, NPAS2, BMAL1 and CRY1 were comparable to the control samples (FIGS. 4C-4E). These results suggested that the level of the CLOCK was reduced in the nucleus, which affects the stoichiometry of the BMAL1/CLOCK dimer in the nucleus. Considering the levels of CRY1 and PER2 level were unaltered we then expected negative feedback loop to be more effective on CLOCK:BMAL1-transactivation. To evaluate this U2OS cells were synchronized with dexamethasone and treated with CLK8, then cells were collected every 6 h to measure the transcriptional and protein levels of core clock components. The oscillatory amplitude of clock gene expression was generally lower in CLK8 treated cells (FIGS. 5A-5K). In particular the protein levels of CLOCK and BMAL1 in the positive arm of the oscillator were reduced (FIGS. 5A-5D). The transcriptional level of Clock was increased to compensate for the reduction in CLOCK protein. Furthermore, CRY1 and PER2, components of the negative arm of the oscillator, showed comparable protein abundance in the presence and absence of the CLK8 (FIGS. 5A-5D) despite significantly reduced transcript level (FIGS.

5E-5K). These results suggested that CLK8 caused a reduction in protein levels in positive arm (BMAL1 and CLOCK) without altering the protein levels in the negative arm (CRY and PER) and therefore cause the reduction in transcriptional level of clock genes (Cry1, Per2, Rev-erb, Roar and Dbp). These results suggested that stabilization of repression arm by CRY and PER by reducing CLOCK:BMAL1 transactivation and leads to enhanced overall circadian amplitude in cell lines.

In Vivo Effect of CLK8 on Mice Liver

All in vitro studies suggested that CLK8 specifically binds CLOCK and inhibit its interaction with BMAL1 interfering with nuclear translocation. To assess its in vivo effect, CLK8 was intraperitoneally (i.p.) administered into mouse at 25 mg/kg. Mice were sacrificed 6 h after the injection and all organs were kept for downstream analysis. We observed a decrease in CLOCK levels in the whole liver cell lysate of the mice liver (FIGS. 6A-6D). On the other hand, the levels of BMAL1 and CRY1 were unaltered (FIGS. 6A-6D). We further analyzed the levels of CLOCK in the cytosolic and nuclear fraction of the mouse liver. We fractionated liver samples from vehicle and CLK8 treated animals euthanized after 6 h of administration, separately isolating cytosolic and nuclear proteins. Proteins, known to be specifically localized in nucleus (Histone-H3) and cytoplasm (Tubulin), were used as controls to evaluate the purity of the fractions (FIGS. 6E-6G).

Figure 6A:
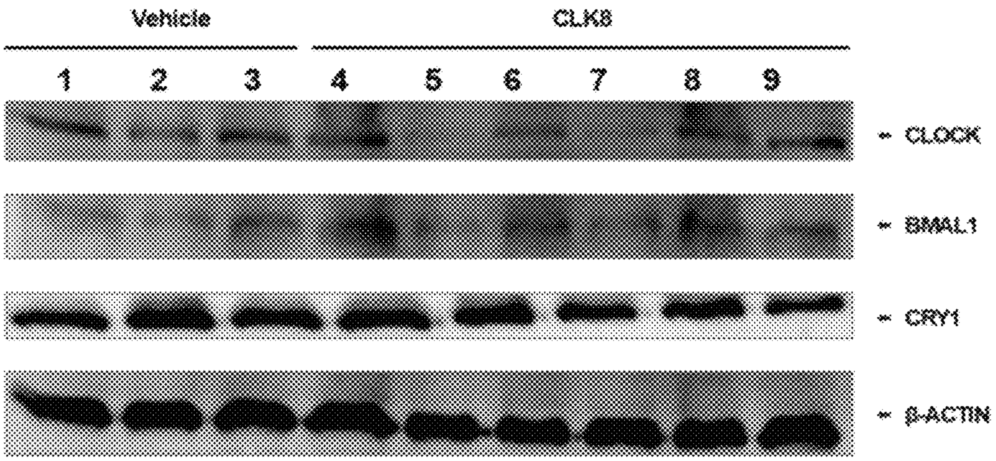
FIGS. 6A-6J are an illustration of the effect of CLK8 in mice liver.
Figure 6B:
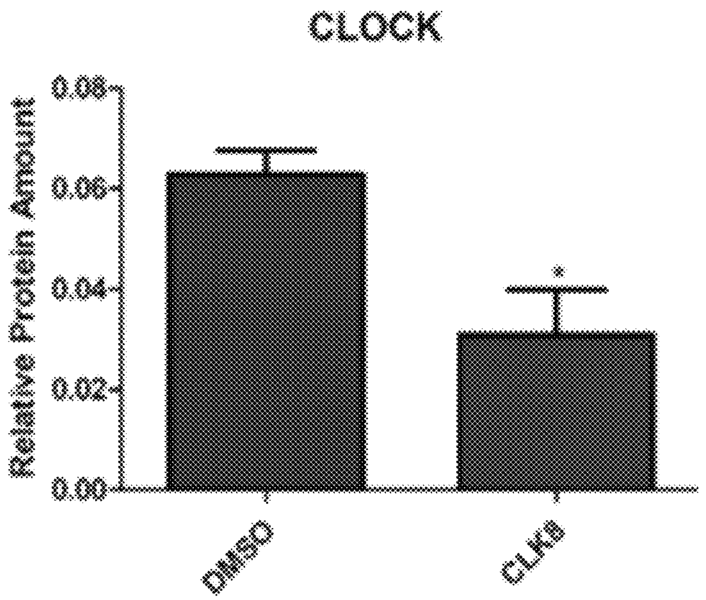
Figure 6C:
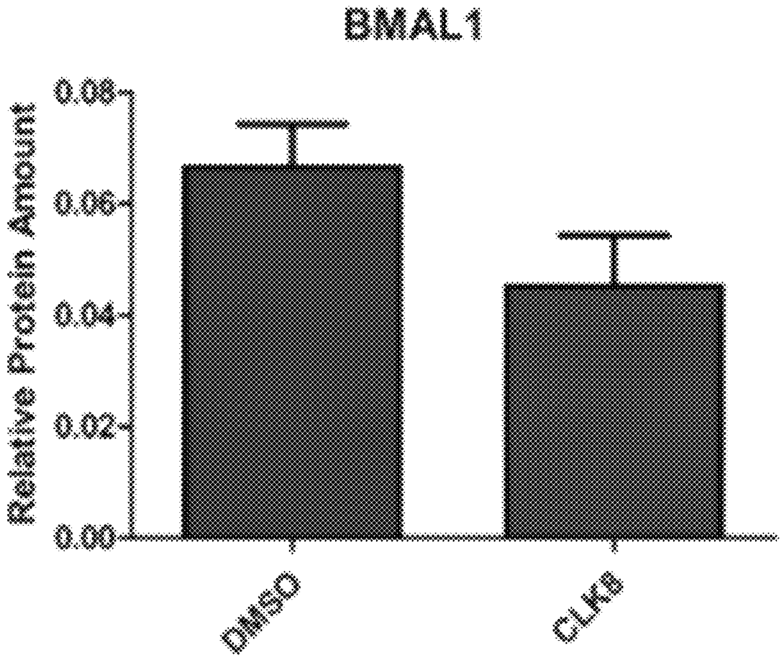
Figure 6D:
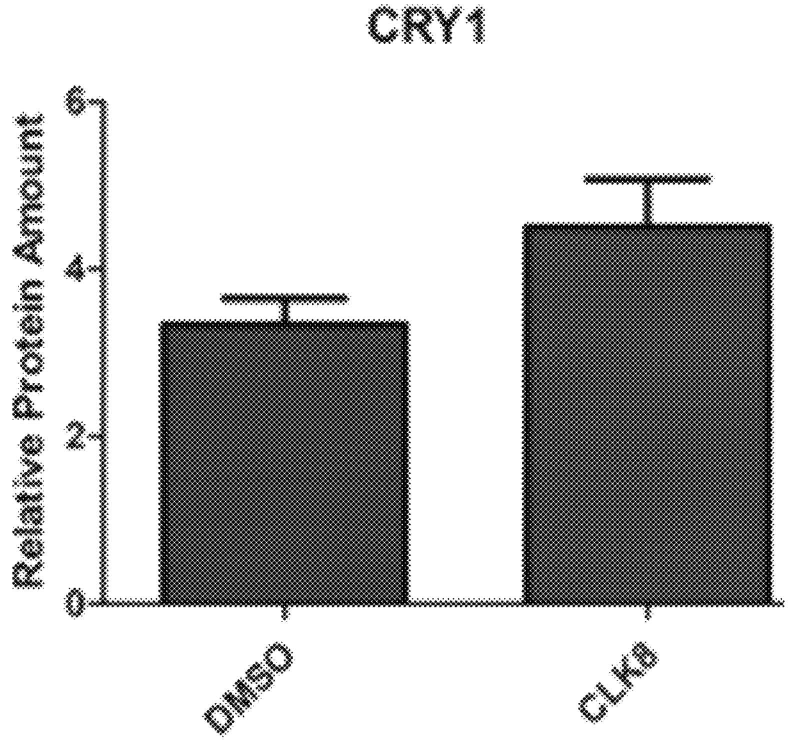
Figure 6E:
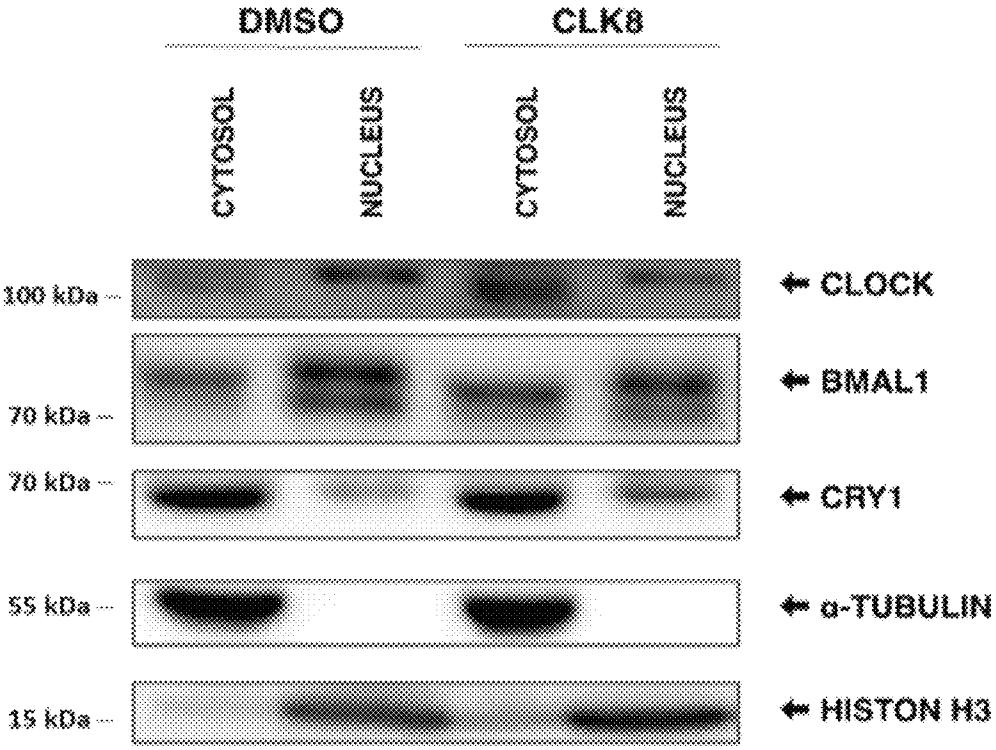
Figure 6F:
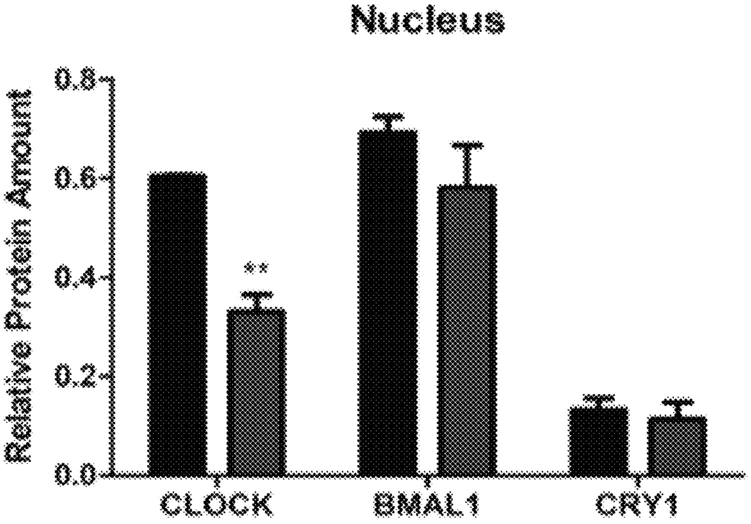
Figure 6G:
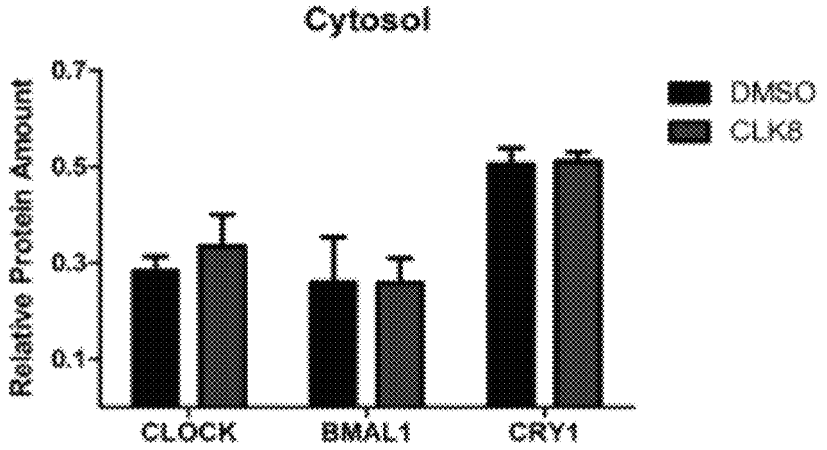
Figure 6H:
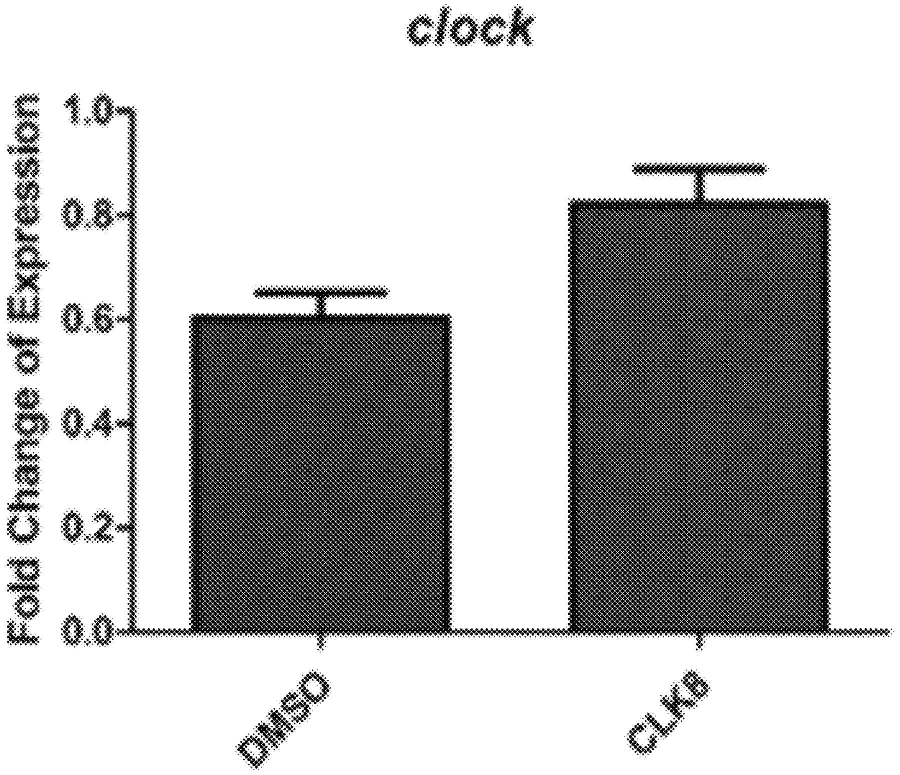
Figure 6I:
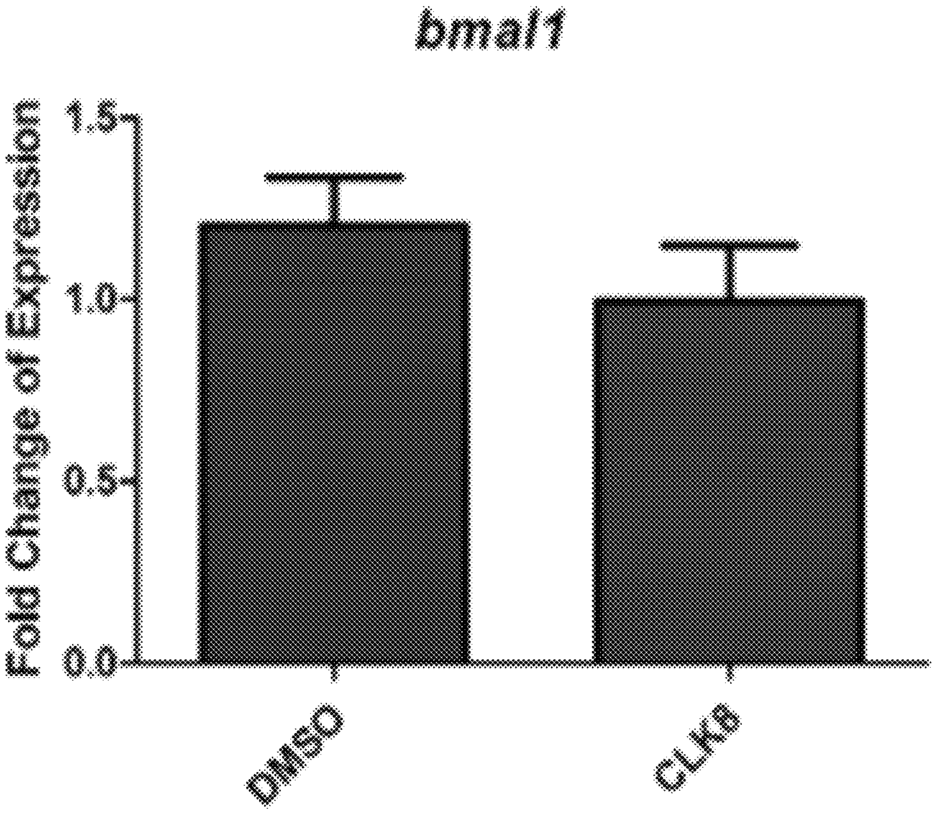
Figure 6J:
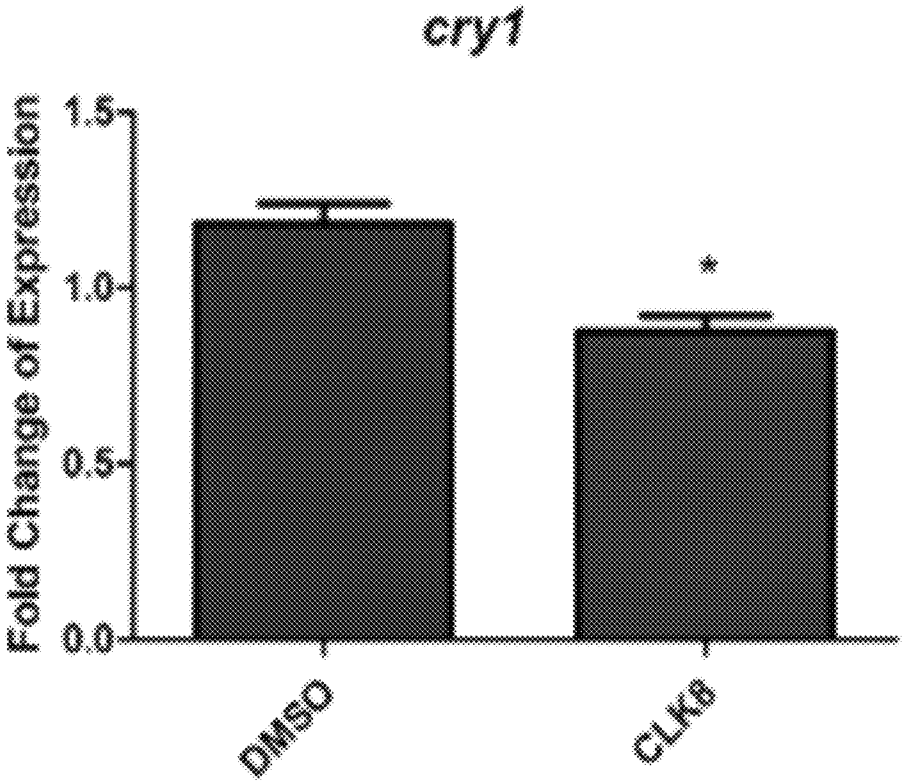

CLOCK abundance in the nucleus was significantly low in animals treated with CLK8 compared to control animals (FIGS. 6E-6G). On the other hand, cytosolic and nuclear BMAL1 and CRY1 were unaltered in CLK8 treated mice liver (FIGS. 6E-6G). To further explore the influence of CLK8 on circadian transcriptional function in vivo, we used qPCR to measure the transcriptional levels of Bmal1, Clock, and Cry1. Only the Cry1 gene's transcriptional level was significantly changed in mice treated with CLK8 compared to the untreated animals (FIGS. 6H-6J). All these in vivo data are consistent with our in vitro data and suggested that CLK8 displays the same phenotype in mice liver.

REFERENCES

Hirota T., Lee, J. W., Lewis, W. G., Zhang, E. E., Breton, G., Liu, X., Garcia, M., Peters, E. C., Etchegaray, J. P., Traver, D., Schultz, P. G., and Kay, S. A. (2010) High-throughput chemical screen identifies a novel potent modulator of cellular circadian rhythms and reveals CKIalpha as a clock regulatory kinase. PLOS Biol 8, e1000559.

Hirota, T., Lee, J. W., St John, P. C., Sawa, M., Iwaisako, K., Noguchi, T., Pongsawakul, P. Y., Sonntag, T., Welsh, D. K., Brenner, D. A., Doyle, F. J., 3rd, Schultz, P. G., and Kay, S. A. (2012) Identification of small molecule activators of cryptochrome. Science 337, 1094-1097.

Isojima, Y., Nakajima, M., Ukai, H., Fujishima, H., Yamada, R. G., Masumoto, K. H., Kiuchi, R., Ishida, M., Ukai-Tadenuma, M., Minami, Y., Kito, R., Nakao, K., Kishimoto, W., Yoo, S. H., Shimomura, K., Takao, T., Takano, A., Kojima, T., Nagai, K., Sakaki, Y., Takahashi, J. S., and Ueda, H. R. (2009) CKI epsilon/delta-dependent phosphorylation is a temperature-insensitive, period-determining process in the mammalian circadian clock. P Natl Acad Sci USA 106, 15744-15749.

Chun, S. K., Jang, J., Chung, S., Yun, H., Kim, N. J., Jung, J. W., Son, G. H., Suh, Y. G., and Kim, K. (2014) Identification and Validation of Cryptochrome Inhibitors That Modulate the Molecular Circadian Clock (vol 9, pg 703, 2014). Acs Chem Biol 9, 1213-1213.

Hu, Y., Spengler, M. L., Kuropatwinski, K. K., Comas, M., Jackson, M., Chernov, M. V., Gleiberman, A. S., Fedtsova, N., Rustum, Y. M., Gudkov, A. V., and Antoch, M. P. (2011) Selenium is a modulator of circadian clock that protects mice from the toxicity of a chemotherapeutic drug via upregulation of the core clock protein, BMAL1. Oncotarget 2, 1279-1290.

Huang, N., Chelliah, Y., Shan, Y., Taylor, C. A., Yoo, S. H., Partch, C., Green, C. B., Zhang, H., and Takahashi, J. S. (2012) Crystal structure of the heterodimeric CLOCK: BMAL1 transcriptional activator complex. Science 337, 189-194.

Dubrovsky Y V, Samsa W E, Kondratov R V. Deficiency of circadian protein CLOCK reduces lifespan and increases age-related cataract development in mice. Aging (Albany NY). 2010; 2 (12): 936-944.

McIntosh, B. E., Hogenesch, J. B., and Bradfield, C. A. (2010) Mammalian Per-Arnt-Sim proteins in environmental adaptation. Annu Rev Physiol 72, 625-645.

Phillips, J. C., Braun, R., Wang, W., Gumbart, J., Tajkhorshid, E., Villa, E., Chipot, C., Skeel, R. D., Kale, L., and Schulten, K. (2005) Scalable molecular dynamics with NAMD. J Comput Chem 26, 1781-1802

Humphrey, W., Dalke, A., and Schulten, K. (1996). VMD: visual molecular dynamics. J Mol Graph 14, 33-38, 27-38.

Morris, G. M., Huey, R., Lindstrom, W., Sanner, M. F., Belew, R. K., Goodsell; D. S., and Olson, A. J. (2009). AutoDock4 and AutoDockTools4: Automated docking with selective receptor flexibility. J Comput Chem 30, 2785-2791.

Lipinski, C. A. (2000). Drug-like properties and the causes of poor solubility and poor permeability. J Pharmacol Toxicol Methods 44, 235-249.

McClung, C. A. (2007). Clock genes and bipolar disorder: implications for therapy. Pharmacogenomics 8, 1097-1100.

Vitaterna, M. H., Ko, C. H., Chang, A. M., Buhr, E. D., Fruechte, E. M., Schook, A., Antoch, M. P., Turek, F. W., and Takahashi, J. S. (2006). The mouse Clock mutation reduces circadian pacemaker amplitude and enhances efficacy of resetting stimuli and phase-response curve amplitude. Proc Natl Acad Sci USA 103, 9327-9332.

Nievergelt C. M., Kripke D. F., Barrett T. B., Burg E., Remick R. A., Sadovnick A. D. Suggestive evidence for association of the circadian genes PERIOD3 and ARNTL with bipolar disorder. Am. J. Med. Genet. B Neuropsychiatr. Genet. 2006; 141B: 234-241.

Mansour H. A., Wood J., Logue T., Chowdari K. V., Dayal M., Kupfer D. J., Monk T. H., Devlin B., Nimgaonkar V. L. Association study of eight circadian genes with bipolar I disorder, schizoaffective disorder and schizophrenia. Genes Brain Behav. 2006; 5:150-157.

Kondratov, R. V., Chernov, M. V., Kondratova, A. A., Gorbacheva, V. Y., Gudkov, A. V., and Antoch, M. P. (2003). BMAL1-dependent circadian oscillation of nuclear CLOCK: posttranslational events induced by dimerization of transcriptional activators of the mammalian clock system. Genes Dev 17, 1921-1932.

CROSS REFERENCE TO THE RELATED APPLICATIONS

This application is the national phase entry of International Application No. PCT/TR2019/051082, filed on Dec. 16, 2019, the entire contents of which are incorporated herein by reference.

SEQUENCE LISTING

The instant application contains a'Sequence Listing which has been submitted in ASCII format via EFS-Web and is hereby incorporated by reference in its entirety. Said ASCII copy is named GBAP222_Sequence Listing.txt, created on Jun. 14, 2022, and is 11,986 bytes in size.

TECHNICAL FIELD

The present invention discloses and claims 2-[2-({12,12-dimethyl-4-oxo-6-phenyl-3,11-dioxatricyclo [8.4.0.0,2,7] tetradeca-1,5,7,9-tetraen-8-yl} oxy) acetamido] benzamide (formula I) as CLOCK-binding small molecule and inhibitor of CLOCK:BMAL1 interaction, and method of using said compound formula I for treating disorders including aging, mood disorders, sleep disorders and diseases related with reduced circadian amplitude. Pharmaceutical compositions comprising formula I and methods for the preparation of formula (I) are also disclosed and claimed.

BACKGROUND

The circadian clock generates a 24-hour rhythm through which physiology and behavior adapt to daily changes in the environment. Many biological processes like hormone secretion, and sleep-wake cycles are controlled by the circadian clock. Therefore, an innate malfunctioning of the circadian clock or a shift between internal circadian rhythm and the external environment can cause various pathologies. Sleep disorders, altered metabolism, obesity, diabetes, mood disorders, cancer and cardiovascular diseases are all linked to an abnormal circadian rhythm. Also, a decrease in the robustness of the circadian rhythm (amplitude decline) is correlated with different pathologies and chronic diseases such as mood disorders and metabolic diseases. Aging is also associated with dampened amplitude and imperfect timing of the circadian rhythm and therefore a weakening of many clock-controlled physiological processes.

The mammalian circadian clock is based on a positive and negative transcription/translation feedback loop (TTFL) in which CLOCK and BMAL1 proteins act as transcriptional activators of Cryptochrome (Cry) and Period (Per) genes, which encode proteins that repress CLOCK-BMAL1 with a periodicity of ~24 h. In the positive arm of the loop, CLOCK and BMAL1 heterodimerize and positively regulate the expression of clock controlled genes including Per and Cry genes. In the negative arm of the loop, the PER: CRY complex along with casein kinase IA translocates into the nucleus, interacts with CLOCK:BMAL1, and inhibits the transcriptional activity of CLOCK:BMAL1, therefore repressing the transcription of Per and Cry and other clock controlled genes. Once PERs and CRYs are degraded, the repression is relieved and a new cycle starts. The second feedback loop consists of RORs and REV-ERBs, which are expressed under the control of CLOCK:BMAL1 and activate and repress the transcription of Bmal1, respectively. A robust and precise rhythm is not generated unless the amount of clock proteins, their localization and their activity are precisely regulated; a process in which several post-translational modifications is involved.

Without a robust and well-aligned circadian rhythm, organisms cannot adapt to environmental changes adequately deafening the evolutionary purpose of the circadian clock. To modify a disrupted circadian rhythm, small molecules are of great priority due to their reversible and time and dose-tunable effects. So far, unbiased screening based on phenotypic changes in the circadian rhythm of reporter cells have resulted in the discovery of multiple clock modulating, small molecules with various circadian phenotypes (Hirota et al., 2010; Isojima et al., 2009). Among these compounds, KL001 binds to CRY and stabilizes it (Hirota et al., 2012). Enhancers of CLOCK:BMAL1 transcriptional activity, and a molecule that augments CRYs repression activity have been detected in high-throughput screening studies utilizing mechanistic approaches (Chun et al., 2014; Hu et al., 2011). Targeting nuclear receptors and protein kinases involved in the circadian clock mechanism has resulted in the identification of different ROR agonists/antagonists, REV-ERB agonists and kinase inhibitors.

In the international patent document WO2018132383A1, small molecule agents that disrupt CRY1-CLOCK-BMAL1 ternary complexes are disclosed. According to this invention, these disrupting agents bind to the secondary pocket of CRY1 and in this way inhibit interaction between the secondary pocket and the CLOCK PAS-B domain. Agents of interest herein are small molecules, polymer, peptides, polypeptides.

Another effective method to identify small molecules that perturb a biological system is structure-based design. Since the crystal structures of clock proteins are now available, this approach can lead to identification of clock modulating compounds targeting clock proteins. The crystal structure of CLOCK:BMAL1 heterodimer reveals that similar domains of CLOCK and BMAL1 (bHLH, PASA,
and PAS-B) interact with each other and provide three protein-protein interfaces (Huang et al., 2012). Different hollows and clefts are present on the surface of each protein, allowing them to interlock to make a stable interaction. Containing a PAS domain, per se, makes CLOCK a druggable target because PAS domains, as internal sensors of living cells, are capable of binding different cofactors (McIntosh, 2010).

Many physiological variables require a robust circadian clock for their proper function. Disturbances in the circadian clock can result in various metabolic diseases and accelerated aging. There is a need for a circadian rhythm controlling molecules and compositions capable of improving circadian rhythm dysfunctions, in particular, a circadian rhythm controlling molecules or compositions capable of amplifying the amplitude of circadian rhythm. It has therefore become increasingly interesting to identify small molecules that can specifically modulate regulatory core clock proteins since they have the potential to manage these diseases. The CLOCK plays a central role as a transcription factor in the circadian pacemaker and makes it an attractive target for therapeutic intervention in aging, sleep disorders and mood disorders. There are evidences that CLOCK be active in circadian rhythm disorders and inactive in healthy subjects, therefore that agents which inhibit CLOCK:BMAL1 interaction be effective in treating circadian rhythm related diseases and disorders (Dubrovsky et al. 2010; Mansour et al., 2006; McClung, 2007; Nievergelt et al., 2006; Vitaterna et al., 2006). It is possible to control circadian rhythm disorders by means of inhibiting the CLOCK:BMAL1 interaction.

Despite advances in drug discovery directed to identifying inhibitors of CLOCK and/or BMAL1 protein activity, there is still a scarcity of compounds that are both potent, efficacious, and selective inhibitors of CLOCK:BMAL1 interaction. Furthermore, there is a scarcity of compounds effective in the treatment and/or prevention of disorders associated with the circadian rhythm. These needs and other needs are satisfied by the present invention.

SUMMARY

According to a first aspect of the invention there is provided a CLOCK-binding compound of formula I or pharmaceutically acceptable salts thereof.

Accordingly, a broad embodiment of the invention is directed to a CLOCK-binding compound of formula I:

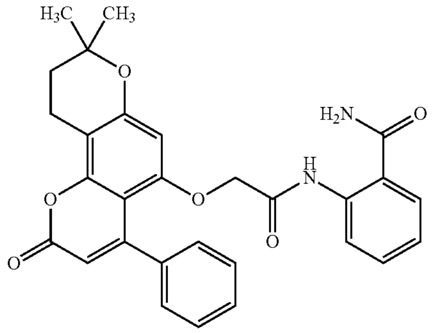 [SMILES: CC1(C)CCc2c(cc(OCC(=O)Nc3ccccc3C(N)=O)c3c(-c4ccccc4)cc(=O)oc23)O1]

The other aspect of the present invention is to provide a CLOCK-binding compound for treating and/or preventing a circadian rhythm associated diseases or disorders, wherein the compound is characterized by inhibiting CLOCK's interaction with BMAL1.

In a further aspect, the present invention relates to a CLOCK-binding compound of the invention for use in reducing strength of positive loop mediated by lowering the CLOCK:BMAL1 level in nucleus and, in turn, transcriptional activity in a mammal.

Another aspect of the present invention is to provide a CLOCK-binding compound capable of controlling circadian rhythm and amplifying circadian rhythm amplitude.

Another embodiment of the present invention relates to a method for identifying a compound for inhibiting the interaction between CLOCK and BMAL1.

The invention can be used for the preparation of a medicament useful in the treatment and/or prevention of disorders due the inhibition of CLOCK:BMAL1 interaction. Yet another objective of the present invention is to provide a pharmaceutical composition comprising a pharmaceutical carrier and a therapeutically effective amount of a compound of formula I, or a pharmaceutically acceptable salt thereof.

This object and other objects of this invention become apparent from the detailed discussion of the invention that follows.

BRIEF DESCRIPTION OF THE DRAWINGS

The present invention is illustrated in the accompanying figures wherein;

FIGS. 1A-1P are an illustration of initial screens for identification of formula I. FIG. 1A shows HEK 293T cells were transfected with pcDNA-Luc and the effect of CLK8 on Luc half-life at 10, 20 and 40 μM of CLK8 were measured. The luciferase signal was monitored after CHX treatment until the luciferase signal reached a plateau. (Data are mean±s.e.m.; n=3 independent experiments). FIGS. 1B-1D show a dose-dependent cytotoxicity of CLK8 in U2OS cell line. All of the measurements were normalized to 0.5% DMSO control. (data are mean±s.e.m.; n=3 independent experiments. FIGS. 1E-1J show continuous monitoring of luminescence rhythms of Bmal1::dluc U2OS and Per1::dluc NIH 3T3 cells to determine dose-dependent effect of CLK8 on circadian rhythm. Amplitude and period parameters are shown in right panel. FIGS. 1K-IM show Bmal1::dluc U2OScells were synchronized at time 0. Two days later (black arrow), cells were treated with 10, 20, and 40 μM of CLK8. Cells treated with 0.5% DMSO were used as a control (luminescence profiles are the means of 3 independent experiments). Amplitude and period parameters (shown in right panel) were obtained by fitting first-order polynomial baseline-subtracted data with sin (damped). The first day was not included in analysis. (data are mean±s.e.m.; n=3 independent experiments). [* p-value<0.05;  p-value<0.01; * p-value<0.001]. (F) MDA MB231 wild type and FIGS. 1N-1P show clock knock-out MDA MB231 cells were transduced with Bmal1::dluc lentiviral particles. At 72 hour posttransduction, the luminescence rhythms of the cells were monitored continuously to determine dose dependent effect of CLK8 on circadian rhythm. Amplitude and period parameters (shown in bottom panel) were obtained by fitting first-order polynomial baseline-subtracted data with sin (damped). (Luminescence profiles are means of 3 independent experiments. data are mean±s.e.m.; n=3 independent experiments.). [* p-value<0.05]

FIGS. 2A-2C are an illustration of specific binding of formula I to CLOCK. FIG. 2A shows a chemical structure of biotinylated FORMULA I (bait). Pull down assay using whole cell lysates of FIG. 2B HEK 293T cells overexpressing Clock and Bmal1 from pSport6 plasmids, FIG. 2C shows U2OS cells. When needed FORMULA I was used as a competitor. (data are representative of 3 independent experiments)

FIGS. 3A-3D are an illustration of the docking results of formula I. FIG. 3A shows a chemical structure of formula I. FIG. 3B shows the best binding mode of FORMULA I to CLOCK with predicted binding energy of −8.2 kcal/mol. FORMULA I enters the hollow between the α2 helix of the bHLH domain and the HB strand of the PAS-A domain of CLOCK. FIG. 3C shows a superposition of FORMULA I and Arg126 of BMAL1 (magenta). FORMULA I and Arg126 of BMAL1 share the same binding region on CLOCK, where Phe80 plays an essential role. Also, the positively charged Lys220 on PAS-A domain of CLOCK contributes in a pi-cation interaction with FORMULA I. FIG. 3D shows a pull down assay using whole cell lysate of HEK 293T cells overexpressing CLOCK-F80A-K220A and BMAL1.

FIGS. 4A-4E are an illustration of reduction of CLOCK and BMAL1 interaction and nuclear localization of CLOCK by FORMULA I. FIGS. 4A-4B show the effect of FORMULA I on the association of CLOCK and BMAL1 were evaluated by co-Immunoprecipitation experiment. Anti-FLAG affinity gel was used to precipitate FLAG-tagged CLOCK together or FLAG-tagged CLOCK-F80A-K220A mutant with BMAL1. The western blot analysis using Anti-BMAL1 and Anti-FLAG antibodies were performed to compare the association of CLOCK and CLOCK-F80A-K220A mutant with BMAL1 in samples with different concentrations of CLK8. Quantification of the blot is shown in bottom panel. The vertical axis indicating the amount of BMAL1 (normalized by CLOCK) in each sample was calculated relative to the DMSO control. FIGS. 4C-4E show unsynchronized U2OS cells were treated with 20 μM of CLK8. Control cells were treated with 0.5% DMSO. Two days later, cells were fractionated and examined by western blot analysis, where CLOCK, NPAS2, PER2, BMAL1 and CRY1 were normalized by α-TUBULIN or HISTON H3. Quantifications are shown in below. (data are mean #s.e.m.;

n=5 independent experiments; western blot data is representative of 5 independent experiments); [* p-value<0.05; ** p-value<0.01;]

FIGS. 5A-5K are an illustration of FORMULA I altered CLOCK protein level in time dependent manner. Confluent U2OS cells were synchronized by 2-hours treatment with dexamethasone (0.1 μM) and medium replaced with fresh medium containing CLK8 or DMSO. Cells were harvested at indicated time points. FIGS. 5A-5D show a time dependent analysis of core clock proteins by Western blot. (mean±SEM, n=3). FIGS. 5E-5K show a qPCR analysis of the core clock genes in a time dependent manner. (Data represent the mean±SEM, n=3 *: p<0.001 : p<0.005, *: p<0.05 versus DMSO control by one-way ANOVA Tukey).

FIGS. 6A-6J are an illustration of the effect of CLK8 in mice liver. FIGS. 6A-6D show after animals were treated with CLK8, they were scarified, and protein lysates were prepared and probed with antibodies for different core clock proteins. FIGS. 6E-6G show mice liver (n=3 for vehicle treated animals and n=5 for CLK8 treated animals) were fractionated and samples were subjected to Western blot analysis. Quantifications are shown in right panel (data are mean±s.e.m.; n=3 independent experiments for the control; n=5 independent experiments for CLK8 treated samples); [** p-value<0.01; one-way ANOVA]. FIGS. 6H-6J show the transcriptional levels of Clock, Cry1 and Bmal1 were measured with qPCR. (data are mean±s.e.m.; n=3 independent for control; n=5 CLK8 treated animals) [* p-value<0.05]. 1, 2, and 3 indicates the animal number used as control (treated with vehicle). The number indicated with 4, 5, 6, 7, 8, and 9 represents animal treated with CLK8.

DETAILED DESCRIPTION OF THE EMBODIMENTS

In the present invention, it is aimed to discover a novel CLOCK-binding small compound using a structure-based approach. As a result, the interaction of a CLOCK-binding compound with CLOCK has been predicted in silico and then demonstrated experimentally.

The CLOCK-binding compound was identified that decreases the interaction between CLOCK and BMAL1 by regulating the translocation of CLOCK into the nucleus both in vivo and in vitro.

Furthermore, it was discovered that, as a result of this interaction, the translocation of CLOCK is regulated by the CLOCK-binding compound resulting in suppression of the function thereof. A decrease in nuclear CLOCK leads the stabilization of the negative arm of the TTFL and, in turn, an enhanced the amplitude of the circadian rhythm with no change in period length.

The present invention relates to a CLOCK-binding compound (formula I).

Unless specified otherwise, the term "formula I" or "compound" or "CLK8" refers to compounds of formula I, prodrugs thereof, salts of the compound and/or prodrug, hydrates or solvates of the compound, stereoisomers, tautomers, isotopically labeled compounds, polymorphs, and derivatives of pharmacophore formula I.

It is an object of this invention to provide a CLOCK-binding compound (named CLK8) having the chemical name 2-[2-({12,12-dimethyl-4-oxo-6-phenyl-3,11-dioxatricyclo [8.4.0.0,2,7] tetradeca-1,5,7,9-tetraen-8-yl} oxy) acetamido] benzamide (IUPAC) as inhibitor of CLOCK:BMAL1 interaction and so inhibitor of transcriptional activity of CLOCK:BMAL1.

In accordance with the purpose(s) of the invention, as embodied and broadly described herein, the present invention relates to a CLOCK-binding compound, capable of inhibiting the interaction between CLOCK and BMAL1 by binding to CLOCK. In this regard, the invention relates to a compound having the following formula I:

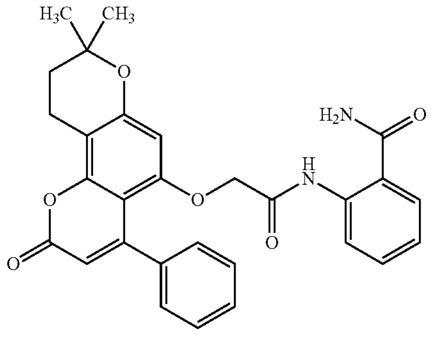 [SMILES: CC1(C)CCc2c(cc(OCC(=O)Nc3ccccc3C(N)=O)c3c(-c4ccccc4)cc(=O)oc23)O1]

or a pharmaceutically acceptable salt thereof.

In a further aspect, the present invention relates to a compound (formula I) that binds to a CLOCK protein and negatively modulate CLOCK:BMAL1 activity.

The present invention relates to a novel CLOCK-binding small molecule that affects the translocation of the CLOCK protein into nucleus through the modulation of the BMAL1 and CLOCK interaction and thus enhances circadian rhythm. CLOCK and BMAL1 are dynamically interacting. When formula I is present, it binds to CLOCK and reduces CLOCK and BMAL1 interaction. Upon binding of formula I to CLOCK, the translocation of the CLOCK into nucleus abolished. Thus, formula I enhances the amplitude of the circadian rhythm.

In one embodiment of the invention, the disclosed compound exhibits selectivity and high affinity for the CLOCK protein. Thus, the inhibition is potent.

In certain aspects, the compound binds to the hollow between the α2 helix of bHLH domain and HB strand of PAS-A domain of CLOCK. With the exception of CRYPTOCHORME other core clock components known as PERIOD, CLOCK and BMAL1 clock proteins contain PAS domains; yet, results confirm the specific binding of the compound to CLOCK.

Binding of the compound to CLOCK inhibits the interaction between the CLOCK and BMAL1, thereby disrupting an existing CLOCK:BMAL1 heterodimer complex. This inhibition results in a reduction in CLOCK:BMAL1 dimerization and, in turn, the translocation of CLOCK into the nucleus through the modulation of the BMAL1 and CLOCK interaction.

Moreover, it is found that the compound affects the amplitude of circadian rhythm with no period change by decreasing the amount of CLOCK in the nucleus without affecting the protein levels in negative arm (CRY-PER2) or BMAL1. According to the invention, the compound enhances circadian rhythm amplitude persistently.

As used herein, the term "inhibit", "inhibition" or "inhibiting" refers to the reduction or suppression of a given condition, symptom, or disorder, or disease, or a significant decrease in the baseline activity of a biological activity or process such as CLOCK:BMAL1 interaction.

The term "a therapeutically effective amount" of a compound of the present invention refers to a non-toxic and sufficient amount of the compound of the present invention that will elicit the biological or medical response of a subject, for example, reduction or inhibition of the protein: protein interaction, or ameliorate symptoms, alleviate conditions, slow or delay disease progression, or prevent a disease or disorder, etc.

All of the various embodiments of the present invention as disclosed herein relates to methods of treating and/or preventing various diseases and disorders as described herein. As stated herein the compound used in the method of this invention are capable of inhibiting the effects of ClOCK: BMAL1 heterodimer complex.

The invention further provides methods for the treatment or prevention of circadian rhythm related disorders and diseases. Non-limiting examples of circadian rhythm disorders include aging, sleep disorders, altered metabolism (metabolic syndromes), obesity, diabetes, mood disorders, cancer and cardiovascular diseases. Mood disorders including major depressive disorder, bipolar I disorder; sleep disorders including circadian rhythm sleep disorders such as shift work sleep disorder, jet lag syndrome, advanced sleep phase syndrome, non-24-hour sleep-wake syndrome, irregular sleep-wake rhythm and delayed sleep phase syndrome.

Moreover, the invention relates to a pharmaceutical composition comprising such compounds, uses and methods of use for such compounds in the treatment and/or prevention of disorders associated with the circadian rhythm. In other embodiment of the present invention, a pharmaceutical composition comprising the compound is useful in the treatment and/or prevention of circadian rhythm related diseases and disorders due the inhibition of CLOCK:BMAL1 interaction.

The present invention relates to pharmaceutical compositions comprising a pharmaceutical carrier and a therapeutically effective amount of a compound of formula I, or a pharmaceutically acceptable salt thereof.

The present invention also relates to pharmaceutical compositions to treat and/or prevent a CLOCK-mediated disorder, such as different metabolic syndromes during in aging, mood disorders and diseases related to dampened the circadian rhythm. With age, not only the sleep-wake rhythm, secretion rhythm of hormones, such as melatonin involved in deep body temperature and sleep, are known to reduce a variety of physiological rhythms, biological clock is involved in sleep disorders associated with aging.

In one aspect, the disclosure relates to a method for the manufacture of a medicament for inhibiting CLOCK and BMAL1 interaction in a mammal comprising combining a therapeutically effective amount of a disclosed compound with a pharmaceutically acceptable carrier or diluent.

The present invention provides a method for identifying a compound for inhibiting the interaction between CLOCK and BMAL1. The method can be established using systems for pharmaceutical screening that are well known in the art.

In one aspect, the present invention provides a method for identifying a compound that inhibits the interaction between CLOCK and BMAL1, wherein the method comprises contacting a compound with CLOCK protein under conditions allowing for the interaction of the compound with CLOCK and/or BMAL1, and determining whether the compound inhibits the interaction between CLOCK and BMAL1 by using a system that uses a signal and/or a marker generated by the interaction between CLOCK and BMAL1 to detect presence or absence or change of the signal and/or the marker. The term "signal" as used herein refers to a substance that can be detected directly by itself based on the physical properties or chemical properties thereof. The term "marker" refers to a substance that can be detected indirectly when the physical properties or biological properties thereof are used as an indicator.

These examples are intended to representative of specific embodiments of the invention and are not intended as limiting the scope of the invention.

SPECIFIC EMBODIMENTS

In these embodiments, a structure-based design was applied to find small molecules that specifically bind to the circadian core CLOCK protein. After identifying candidate molecules by virtual screening, experimental studies lead to discover a compound (formula I) that specifically binds to CLOCK. It regulates the interaction between CLOCK and BMAL1 by interfering with the translocation of CLOCK into the nucleus both in vivo and in vitro. Further studies indicated that formula I enhances the amplitude of the circadian rhythm at the cellular level by stabilizing the negative arm of the transcriptional/translational feedback loop without affecting the period length.

EXAMPLES

Example 1 in Silico Search for Compounds that Interact with CLOCK

Molecular Dynamics of CLOCK

The initial structure of the CLOCK protein was obtained from the Protein Data Bank (PDB ID: 4F3L) (Huang et al., 2012). Molecular Dynamic (MD) simulations were carried out by NAMD (Phillips et al., 2005) software using CHARMM force field. First, the protein structure files (PSF) for MD simulations were prepared by VMD (Humphrey et al., 1996) after removing crystallographic water molecules and adding hydrogen atoms using AutoDockTools4 (Morris et al., 2009). Using the psfgen package, atom and residue names were replaced with the ones recognized by NAMD. Then, the structure was dissolved in a water-box and the system was ionized. In the first 10000 steps of minimization, the backbone was fixed. Further 10,000 steps of minimization were performed on all atoms with no pressure control. Subsequently, the system was brought to physiological temperature (310 K) by 10 K increments with 10 ps simulation for each increment in which alpha-carbons were restrained. The constraint scaling decreases from 1 to 0.25 kcal/(mol Å2) in 0.25 increments, with each increment being 5,000 steps. Further 90,000 steps with zero constraint scaling were performed as the final part of energy minimization before RMSD of protein was converged and stabilized. MD simulation for equilibrium was performed using the Langevin dynamics at 310 K with a damping coefficient of 5 ps-1, 1 atm constant pressure and the Langevin piston period and decay of 100 and 50 fs respectively. The bonded interactions, the van der Waals interaction with 12 Å cutoff, and the long-range electrostatic interactions with the particle-mesh Ewald (PME) were considered in the calculations of the forces acting on the system. At the end, the RMSD of the CLOCK backbone with respect to its initial structure showed that the equilibrium was reached after 3-4 ns. The final structure of the CLOCK after 10 ns of simulation was used as the receptor for docking step.

Docking Setup

After MD simulations, water molecules of the system were deleted and the PDBQT file of the receptor, CLOCK, was prepared using AutoDockTools4 (Morris et al., 2009). The library of commercially available small molecules (by Ambinter) was filtered according to "Lipinski's Rule of Five" (Lipinski, 2000) considering a maximum limit of one violation. Finally, approximately 2 million small molecules were selected for docking. PDBQT files of ligands were prepared by means of an automated script in Python language. We used AutoDock Vina for estimating protein-ligand affinity and predicting the best binding conformations of the compounds. The search space was defined to include the whole CLOCK protein to perform blind docking. The exhaustiveness was set as the default. Ultimately, the compounds were ranked based on their binding affinities (kcal/mol). The protein-compound interactions of the top 500 hit compounds were visually examined by the Discovery Studio Visualizer. The threshold value for hydrogen bonding was set as 3.4 Å and the accessible surface area was created considering a radius of 1.4 Å for solvent molecules. In the process of selecting hit molecules, compounds with docking positions far from CLOCK:BMAL1 protein interfaces were eliminated. A final number of 100 compounds with affinities ranging from −7 to −10 kcal/mol was reached by considering features such as favorable shape complementarity and diversity in binding region and chemical properties. The top 100 compounds were then tested experimentally.

Example 3 Cell Cytotoxicity Test

The toxicity of the compounds was assessed by MTT-based assay using immortalized human osteosarcoma (U2OS) cells treated with different compounds at different concentrations. Cell viability was measured with MTT-based cell cytotoxicity test. U2OS cells were seeded on 96-well plate with $4\times10^3$ cell/well density. Two days later, the cells were treated with an appropriate amount of different small molecules. Control cells were treated with 0.5% vehicle (DMSO). After 48 hours, the media was replaced with a 20% solution of 5 mg/ml MTT in DMEM. After 4 hours of incubation, the media was discarded and a 1:1 solution of ethanol and DMSO was used to dissolve the formazan crystals. Cell viability was measured as stated in Sigma-Aldrich product information.

Compounds with a relative cell viability of less than 80% at 1.25 μM were eliminated. The final concentration of a non-toxic compounds for in vitro experiments was set to the maximum concentration at which it had at least 80% relative cell viability. Ultimately, 72 compounds were statistically identified as non-toxic and used for the next characterization step.

Example 4 Mammalian Two-Hybrid Assay

The procedure was carried out according to Checkmate-Promega's protocol. Samples were examined in triplicate sets in a 96-well plate. HEK293T cells with the density of $4\times10^4$ cell/well were transfected with 50 ng of pG5-luc, 50 ng of pACT-mBmal1, 50 ng of pBind-hsClock plasmids and 0.5 ng of pRL-TK for normalization. Following the transfection, the cells were treated with different concentrations of small molecules. Control cells were treated with 0.5% vehicle (DMSO).

Ultimately, luminescence was measured using Dual-Luciferase Reporter Assay System (Promega) with Fluoroskan Ascent FL plate reader.

Example 5 Real-Time Monitoring of Circadian Rhythm

We used Bmal1::dluc U2-OS and Per1::dluc NIH 3T3, and continuously monitored the bioluminescence to record circadian rhythm. This experiment was performed in 96-well plates (triplicates) and 35-mm dishes (duplicates) in the secondary screen and detailed characterization steps respectively. Briefly, cells were seeded to reach confluency. A day after, the medium was replaced with DMEM containing 0.1 μM Dexamethasone to synchronize cells. Two hour later, 0.1 mM of Luciferin was freshly added to the recording medium (low glucose DMEM powder (with L-glutamine) supplemented with 10 mM HEPES, 0.35 mg/ml sodium bicarbonate, 3.5 mg/ml D-(+)-glucose powder, 5% FBS, 0.1 mM NEAA, 100 U/ml penicillin and 100 mg/ml streptomycin). Then, the medium was replaced with recording medium containing appropriate amount of each compound. Control cells were treated with 0.5% vehicle (DMSO). For a detailed characterization of CLK8, whenever required, and without any further medium change, small molecule treatment was postponed to two days after bioluminescence recording started. The 96-well plates were covered and bioluminescence was monitored by Synergy H1 Hybrid Multi-Mode Reader every 32 minutes. Similarly, we sealed the 35-mm plates with vacuum grease prior to mounting them on a LumiCycle luminometer (Actimetrics). Bioluminescence was recorded every 10 minutes for 4-6 days. Raw data (counts/sec) were plotted against time. The period and amplitude parameters were obtained using LumiCycle Analysis software (Actimetrics). First, the raw data was baseline fitted (n=1), and then the baseline-subtracted data was fitted to a sine wave (damped). The first day's data was excluded from the analysis due to transient perturbations of luminescence after the medium change.

Example 6 Pull-Down Assay

HEK293T cells were transiently transfected with tag-free hsClock and mBmal1. After 48 hours of transfection, cells were harvested and whole cell lysate was prepared with ice-cold lysis buffer (50 mM Tris-HCl pH 7.4, 2 mM EDTA, 1 mM $MgCl_2$, 0.2% NP-40, 1 mM sodium orthovanadate, 1 mM sodium fluoride and protease inhibitor cocktail) followed by centrifugation at 7000×g at 4° C. for 10 minutes. Lysate was diluted with ice-cold 2× binding buffer (100 mM Tris-HCl pH 7.4, 300 mM NaCl, 0.2% NP-40, 2 mM sodium orthovanadate, 2 mM sodium fluoride, and protease inhibitor cocktail) 27. The lysate was divided into three fractions to be treated with either DMSO, or 20 μM of bitoinylated-CLK8 (bait) with or without 200 μM CLK8 (competitor). The lysate-compound samples were incubated and mixed continuously at 4° C. for 1 hour. After equilibrating NeutroAvidin Agarose resin (Thermo Scientific) with lysis buffer, the lysate-compound mixture and NeutroAvidin Agarose resin were incubated and mixed continuously at 4° C. overnight. The beads were washed four times with 1× binding buffer. To elute the bound proteins Laemmli buffer was added and samples were heated at 95° C. for 7 minutes. The pull-down precipitates were subjected to SDS-PAGE and transferred to a PVDF membrane (Millipore). Anti-CLOCK (Bethyl) and anti-BMAL1 (Santa Cruz Biotechnology) antibodies were used to detect CLOCK and BMAL1 proteins respectively. The LC-MS/MS examination of the pull-down precipitates was performed in Koc University's Proteomics Facility. Bitoinylated-CLK8 and CLK8 were synthesized by Enamine, Ukrine.

Example 7 Co-Immunoprecipitation

HEK 293T cells co-expressing wild type or F80A-K220A mutant FLAG-tagged Clock together with tag-free Bmal1 were lysed with ice-cold lysis buffer (50 mM Tris-HCl pH 7.7, 150 mM NaCl, 0.1% Triton X-100, 1 mM PMSF and protease inhibitor cocktail) and centrifuged at 15000×g at 4° C. for 20 minutes. DMSO and different concentrations of CLK8 were added to the whole cell lysate. The mixtures were incubated with anti-FLAG M2 affinity gel (Sigma-Aldrich) at 4° C. overnight with continuous mixing. After three wash steps, bound proteins were eluted with Laemmli buffer heated at 95° C. for 7 minutes. CLOCK and BMAL1 were detected by monoclonal anti-FLAG M2 antibody (Sigma-Aldrich) and anti-BMAL1 (Santa Cruz Biotechnology) respectively. The amount of co-precipitated BMAL1 was normalized with the amount of precipitated CLOCK.

Example 8 mRNA and Protein Analysis

Unsynchronized Bmal1::dluc U2OS cells were seeded on 6-well dishes. Confluent cells were treated with an appropriate amount of CLK8 for 48 hours. Control cells were treated with 0.5% vehicle (DMSO). After harvesting the cells, mRNAs were isolated (RNeasy, QIAGEN) and converted to cDNA (Thermo Scientific). Finally, cDNAs were subjected to SYBR Green-based RT-qPCR assay. PRLP0 was used as an internal control. The primers used in RT-qPCR are listed in Table 2. For western blot analysis RIPA buffer was used to prepare whole cell lysates. The amount of protein for each sample was normalized to the β-ACTIN amount detected by β-Actin antibody (Cell Signalling).

TABLE 2

Primers for the site-directed mutagenesis of CLOCK. Bold indicates the mutated codon.

| Gene | Forward Sequence | Reverse Sequence |
|---|---|---|
| F80A-hsClock | CAGAAAAGCATTGAT**GCT**TTACGAAAAC ATAAAGAAATCACTGCACA (SEQ ID NO: 3) | CTGTGCAGTGATTTCTTTATGTTTTCGTA AAGCATCAATGCTTTTCTG (SEQ ID NO: 4) |
| K220Ahs Clock | GTAAAATTTATAGGAAATTTCGCATCTTT AAACAGTGTATCC (SEQ ID NO: 5) | GGATACACTGTTTAAAGATGCGAAATTT CCTATAAATTTTAC (SEQ ID NO: 6) |

Example 9 Luciferase Degradation Assay

The procedure was similar to the one described in the previous study (Hirota et al., 2012). Briefly, HEK 293T cells were seeded in triplicates in opaque 96-well plates 24 hours prior to transfection. Cells were transiently transfected with 10 ng of pcDNA-dluc plasmid. After 24 hours, cells were treated with different concentrations of CLK8 or DMSO. A day later, luciferin and HEPES (pH 7.2) were added to the medium to the final concentrations of 0.4 mM and 10 mM respectively and incubated for one hour. Subsequently, protein synthesis was ceased by CHX treatment and the luminescence signal was recorded by Synergy H1 Hybrid Multi-Mode Reader for 20 hours. The results were first normalized and then fitted to one-phase decay to calculate the half-life of Luciferase protein.

Example 10 Transactivation Assay

HEK 293T cells with the density of $4\times10^4$ cell/well were transfected with 50 ng of mPer1-luc, 50 ng of Sport6-Bmal1 and 125 ng of Sport6-Clock (wild type) or 125 ng of Sport6-Clock (F80A-K220A) plasmids and 0.5 ng of pRL-TK for normalization. The same experiment was also performed using Flag-tagged constructs of CLOCK instead. Dual-Luciferase Reporter Assay System (Promega) was used to measure the luminescence by Fluoroskan Ascent FL plate reader.

Example 11 Site-Directed Mutagenesis

Site-directed mutagenesis of Sport6-Clock and pCMV-Flag-Clock was performed using platinum Pfx DNA polymerase (Invitrogen) as described in the product's manual. The primer sets are listed in Table 2.

Example 12 Cytosol-Nuclear Fractionation

U2 OS cells treated with 20 μM CLK8 and 0.5% DMSO were used for fractionation analysis. The $4\times10^5$ was suspended in 500 ul cytosolic lysis buffer (10 mM HEPES pH 7,9, 10 mM KCl, 0.1 mM EDTA, 0.05% NP40 with protease inhibitors) and incubated on ice for 10 minutes. The lysate was centrifuged for 3 minutes at 3000 rpm at 4° C. The resulting supernatant was centrifuged one more time and supernatant collected as cytosolic fraction. On the other hand, the resulting pellet from lysate centrifugation was suspended in nuclear lysis buffer (20 mM HEPES pH 7.9, 0.4 M NaCl, 1 mM EDTA, 10% glycerol with protease inhibitors) and sonicated 2 times 10 seconds with 60% power. After centrifuge at 15 000 g for 5 minutes at 4° C., supernatant was collected as nuclear fraction. Collected fractions were used for Western Blot analysis. Fractionation efficiency was checked with Western Blot by using tubulin (Sigma T9026) as cytosolic marker and Histone-H3 (abcam ab1791) as nuclear marker.

Example 13 Lentivirus Production and Transduction

HEK 293T cells at 75-85% confluency were transfected with 10 ng of pLV6-Bmal-luc plasmid, 9 ng of pCMV-AR8.2dvpr packaging vector and 1 ng of pCMV-VSVG envelope vector for 16 h. Next day, the medium was replaced with fresh growth medium. As lentiviral particles were harvested at 72-hour and 96-hour post-transfection. Clock-deficient and wild type MDA MB231 cells were transduced with Bmal1-luc lentiviral particles for 16 h. Medium was replaced fresh growth medium and transduction was repeated one more time. At 72-hour post-transduction, the circadian rhythms of cells monitored using Lumicycle.

Example 14 In Vivo Studies in Mouse Liver

Male C57BL/6J mice, 8 weeks of age, weighing 18-24 g were treated with two different single doses of CLK8 (25 mg/kg n=5 per each dose) intraperitoneally. Control mice (n=3) were only treated with vehicle (DMSO:Cremophor EL: 0.9% NaCl; 2.5:15:82.5, v/v, i.p.). Water and food were provided ad libitum throughout the experiments. Six hours after injection, mice were sacrificed by cervical dislocation. Liver tissues were removed, frozen in liquid nitrogen and stored at −80° C. until further processing.

Example 15 Quantification of Western Blot

All Western blots were obtained from Bio-Rad ChemiDoc Imaging System and the amount of each protein was quantified using Image Lab Software applying volume tools.

Example 16 Statistical Analysis

GraphPad Prism5 was used to assess statistical significance by two-tailed student's t-test. Biological replica were at least n=3 for all of the experiments. [*p-value<0.05,  p-value<0.01, * p-value<0.001.]

Results

The Effect of Hit Compounds on CLOCK:BMAL1 Interaction and Circadian Rhythm

Although the mammalian two-hybrid system (MTHS) is not a quantitative assay that is used to measure the degree of interaction between two proteins, we initially used MTHS to identify the compounds that significantly alter the interaction between CLOCK and BMAL1. Twenty four compounds significantly altered the CLOCK:BMAL1 interaction without changing the protein level (data is not shown), suggesting that they might modulate the positive feedback loop at the molecular level.

We then assessed the effect of these compounds on the circadian rhythm of U2-OS cells stably expressing Bmal1::dluc. The molecules had different effects on the circadian rhythm and were classified accordingly; amplitude-enhancers (9 compounds), period lengtheners (2 compounds), and amplitude-reducers (2 compounds). Subsequent to a dose response validation, only four compounds passed the secondary screening step successfully. To assess the specificity of these four compounds on different genetic background for the circadian rhythm, NIH 3T3 cells stably expressing Per1::dluc were subjected to these four compounds. Two compounds (one of them is CLK8) displayed the same phenotypic changes in both cell lines, suggesting that the core clock mechanism had been affected. The amplitude-enhancing compound, CLK8, was selected for further characterization. None of the amplitude-enhancing small molecules identified so far has affected the positive or negative TTFL of the circadian clock directly.

Before following the experimental procedure further, to assure that CLK8 did not interfere with the luminescence signal itself we examined the degradation rates of LUC in HEK293T cells transfected with pcDNA-Luc and treated with CLK8. The half-life of LUC was unchanged in cells treated with CLK8 confirming luminescence signal as an independent and consistent measuring tool. Thus, the compound likely modulates CLOCK:BMAL1 activity.

The Effect of CLK8 on Circadian Rhythm

The maximum concentration of CLK8 used for in vitro experiments with cell viability higher than 80% was 40 μM and was not toxic to the U2OS cell line (FIG. 1A). Investigations into the effect of CLK8 on the circadian rhythm revealed that CLK8 enhances the amplitude of human U2OS cells stably expressing the Bmal1 promoter-driven luciferase reporter and performed kinetic bioluminescence assays to assess clock function (U2OS-Bmal1::dLuc) and mouse NIH 3T3 cells stably expressing the Per1 promoter-driven luciferase reporter (NIH 3T3-Per1::dLuc) in a dose dependent manner and no period changes were observed in both cell lines (FIGS. 1B-1G). We subsequently decided to monitor the reporter rhythm before and after small molecule treatment to better understand the effects of this compound. U2OS-Bmal1::dLuc cells were synchronized and the reporter rhythms were recorded for two days (FIGS. 1H-1J). Then, different doses of CLK8 were added to cells without replacing the media to prevent any phase resetting (31). Bioluminescence rhythms were recorded for four more days. The luminescence profiles of all the samples were the same until treatment with the small molecule. Compared to the DMSO control, CLK8 advanced the phase of the first trough right after treatment. The CLK8 was able to enhance the amplitude by more than 50% at 10 μM (FIGS. 1H-1J). We analyzed the effect of CLK8 on the Bmal1::dluc knock-in reporter in Clock-deficient and wild type MDA MB231 cells. CLK8 was able to enhance amplitude in wild type MDA MB231 cells (FIGS. 1K-1M) while CLK8-mediated increase in Bmal1-luc intensity was abolished in the Clock knockout cells at different concentrations of CLK8 (FIGS. 1N-IP). These results suggested that the molecule specifically binds CLOCK and results in amplitude enhancement.

Specific Binding of CLK8 to CLOCK

Once CLK8 was identified as a promising molecule, its physical binding to CLOCK was assessed by pull-down assay using biotinylated CLK8 as bait. The biotinylated CLK8 was synthesized by Enamine, a chemical supplier in Ukraine (FIG. 2A).

Whole cell lysate of HEK293T cells overexpressing CLOCK and BMAL1 were incubated with biotinylated CLK8 in the absence and presence of the competitor (CLK8). CLOCK was precipitated with biotinylated CLK8 but not in the presences of the free CLK8 (unbiotinylated CLK8) (FIG. 2B). The results showed that CLK8 specifically binds to CLOCK. Moreover, to eliminate any artifact of an overexpressed system, whole cell lysate of U2OScells expressing endogenous levels of CLOCK (and BMAL1) were used in a pull-down assay. The difference in the amount of CLOCK between the input and the sample precipitated with biotinylated CLK8 revealed that CLK8 has high affinity for CLOCK (FIG. 2C). Except BMAL1, which was always co-precipitated together with CLOCK (although in very low amounts), none of the other core clock components were detected as a target for CLK8 (FIG. 2C) including NPAS2, a homologue of the CLOCK gene. (human CLOCK nucleotide sequence; SEQ ID No: 1)

The next step was to check for off-targets of CLK8. Accordingly, LC tandem mass spectrometry was used to further analyze the precipitated proteins. Since the amount of precipitated endogenous CLOCK was insufficient to be detected in LC-MS/MS, whole cell lysate of HEK 293T cells overexpressing CLOCK and BMAL1 were used for LC-MS/MS. We determined proteins that potentially bind to CLK8 by utilizing a minimum threshold for peptide spectrum matches and coverage equal to those of the main target, CLOCK. We also excluded proteins that have been detected in negative controls of the CRAPome database (32), assuming them as abundant sticky proteins. In the presence of a competitor, CLOCK was not detected in MS/MS, which explicitly showed the specificity of the binding. BMAL1 was detected in lower amounts when a competitor was present. The decrease in the amount of NAV2 in the presence of the competitor introduced it as a possible off-target of CLK8 (Table 1).

TABLE 1

Potential targets of CLK8.

| | Protein | Peptide spectrum matches Competitor (μM) 0 | 200 |
|---|---|---|---|
| CLOCK | Circadian locomoter output cycles protein kaput | 42 | — |
| BMAL1 | Aryl hydrocarbon receptor nuclear translocator-like protein 1 | 56 | 46 |
| NAV2 | Neuron navigator 2 | 263 | 188 |

The docking results showed that FORMULA I (FIG. 3A) binds to the hollow created between the $\alpha 2$ helix of the bHLH domain and the HB strand of the PAS-A domain of CLOCK (FIG. 3B). Based on MD results of the CLOCK: BMAL1 heterodimer, this hollow is where Arg126 of BMAL1 enters and interacts with Phe80 of CLOCK, a conserved hydrophobic core residue on the $\alpha 2$ helix of the bHLH domain (FIGS. 3B-3C). Phe80, according to docking results, is also involved in the interaction between CLOCK and CLK8. Lys220 is another residue that plays an important role in the interaction of CLOCK and FORMULA I (also referred as CLK8) by offering a cation-pi interaction. To confirm the binding site, we replaced Phe80 and Lys220 of CLOCK with Ala by site-directed mutagenesis using appropriate primers. After generating the double mutant (CLOCK-F80A-K220A) we first determined the effect of the mutations on the functions of CLOCK by transactivation assay. To evaluate the functional consequences of these mutations on clock function, we monitored the activity of Per1::luciferase using CLOCK:BMAL1 and Clock-F80A-K220A/Bmal1 in HEK 293T cells. Analysis of the result showed both wild type and mutant clock had same degree of the activation on Per1::luciferase reporter along with BMAL1. Consequently, we used HEK 293T cells overexpressing CLOCK-F80A-K220A and BMAL1 to verify the predicted binding site of CLK8. We performed a pull-down assay using biotinylated CLK8 in the absence and presence of the competitor (CLK8). The results clearly indicated that mutant CLOCK did not precipitate with biotinylated CLK8 to the same extent as wild type CLOCK (FIG. 3D). Besides, the minute amount of precipitated mutant CLOCK did not disappear in the presence of the competitor (CLK8) suggesting the binding of CLK8 to the computationally predicted region (FIG. 3B). Notably, BMAL1 didn't appear in blot as in the case of the pull down experiment with the wild type clock (FIG. 3D) suggesting that BMAL1 comes with wild type CLOCK rather than non-specific binding to the molecule.

Investigation of the Interaction Between CLOCK and BMAL1 in the Presence of CLK8

Mammalian two-hybrid results implied that CLK8 reduces the interaction between CLOCK and BMAL1. To test the effect of this molecule on the interaction between them, a co-immunoprecipitation assay was used. HEK 293T cells were transfected with plasmids encoding Flag-tagged CLOCK and BMAL1. An Anti-FLAG resin was used to precipitate FLAG-CLOCK at 10 UM and 40 μM of CLK8. While FLAG-CLOCK was precipitated to the same extent in all samples, the amount of BMAL1 reduced as the concentration of CLK8 increased (FIGS. 4A-4B). The results suggested that the interaction between CLOCK and BMAL1 decreases as the concentration of CLK8 increases (FIGS. 4A-4B). If this was true, we would expect the interaction between CLOCK F80A-K220A and BMAL1 to remain unaffected in the presence of CLK8. We then repeated pulldown experiment side by side using both mutant and wild type CLOCK. Results showed the BMAL1 and CLOCK interaction was reduced in the presence CLK8 while the interaction between CLOCK-F80A-K220A and BMAL1 was not affected even at 40 μM CLK8 (FIGS. 4A-4B). This data suggests that CLK8 interferes with the CLOCK and BMAL1 interaction.

The Effect of CLK8 on Subcellular Localization of CLOCK

The localization and degradation of CLOCK is regulated by its direct interaction with BMAL1 (Kondratov et al., 2003). We hypothesized the inability of CLOCK binding to BMAL1 in the presence of the CLK8 molecule might alter subcellular localization of the CLOCK protein (SEQ ID NO: 2). To test that U2OS cells treated with 20 μM of CLK8 and cells were fractionated by isolating cytosolic and nuclear proteins. Proteins, specifically localized in the nucleus (Histone-H3) and cytoplasm (Tubulin), were used as controls to evaluate the purity of the fractions (FIGS. 4C-4E). Results indicated that the translocation of the CLOCK into the nucleus was affected the by the presence of CLK8 when compared to the control samples. The level of PER2, NPAS2, BMAL1 and CRY1 were comparable to the control samples (FIGS. 4C-4E). These results suggested that the level of the CLOCK was reduced in the nucleus, which affects the stoichiometry of the BMAL1/CLOCK dimer in the nucleus. Considering the levels of CRY1 and PER2 level were unaltered we then expected negative feedback loop to be more effective on CLOCK:BMAL1-transactivation. To evaluate this U2OS cells were synchronized with dexamethasone and treated with CLK8, then cells were collected every 6 h to measure the transcriptional and protein levels of core clock components. The oscillatory amplitude of clock gene expression was generally lower in CLK8 treated cells (FIGS. 5A-5K). In particular the protein levels of CLOCK and BMAL1 in the positive arm of the oscillator were reduced (FIGS. 5A-5D). The transcriptional level of Clock was increased to compensate for the reduction in CLOCK protein. Furthermore, CRY1 and PER2, components of the negative arm of the oscillator, showed comparable protein abundance in the presence and absence of the CLK8 (FIGS. 5A-5D) despite significantly reduced transcript level (FIGS. 5E-5K). These results suggested that CLK8 caused a reduction in protein levels in positive arm (BMAL1 and CLOCK) without altering the protein levels in the negative arm (CRY and PER) and therefore cause the reduction in transcriptional level of clock genes (Cry1, Per2, Rev-erb, Roar and Dbp). These results suggested that stabilization of repression arm by CRY and PER by reducing CLOCK:BMAL1 transactivation and leads to enhanced overall circadian amplitude in cell lines.

In Vivo Effect of CLK8 on Mice Liver

All in vitro studies suggested that CLK8 specifically binds CLOCK and inhibit its interaction with BMAL1 interfering with nuclear translocation. To assess its in vivo effect, CLK8 was intraperitoneally (i.p.) administered into mouse at 25 mg/kg. Mice were sacrificed 6 h after the injection and all organs were kept for downstream analysis. We observed a decrease in CLOCK levels in the whole liver cell lysate of the mice liver (FIGS. 6A-6D). On the other hand, the levels of BMAL1 and CRY1 were unaltered (FIGS. 6A-6D). We further analyzed the levels of CLOCK in the cytosolic and nuclear fraction of the mouse liver. We fractionated liver samples from vehicle and CLK8 treated animals euthanized after 6 h of administration, separately isolating cytosolic and nuclear proteins. Proteins, known to be specifically localized in nucleus (Histone-H3) and cytoplasm (Tubulin), were used as controls to evaluate the purity of the fractions (FIGS. 6E-6G).

CLOCK abundance in the nucleus was significantly low in animals treated with CLK8 compared to control animals (FIGS. 6E-6G). On the other hand, cytosolic and nuclear BMAL1 and CRY1 were unaltered in CLK8 treated mice liver (FIGS. 6E-6G). To further explore the influence of CLK8 on circadian transcriptional function in vivo, we used qPCR to measure the transcriptional levels of Bmal1, Clock, and Cry1. Only the Cry1 gene's transcriptional level was significantly changed in mice treated with CLK8 compared to the untreated animals (FIGS. 6H-6J). All these in vivo data are consistent with our in vitro data and suggested that CLK8 displays the same phenotype in mice liver.

REFERENCES

Hirota T., Lee, J. W., Lewis, W. G., Zhang, E. E., Breton, G., Liu, X., Garcia, M., Peters, E. C., Etchegaray, J. P., Traver, D., Schultz, P. G., and Kay, S. A. (2010) High-throughput chemical screen identifies a novel potent modulator of cellular circadian rhythms and reveals CKIalpha as a clock regulatory kinase. PLOS Biol 8, e1000559.

Hirota, T., Lee, J. W., St John, P. C., Sawa, M., Iwaisako, K., Noguchi, T., Pongsawakul, P. Y., Sonntag, T., Welsh, D. K., Brenner, D. A., Doyle, F. J., 3rd, Schultz, P. G., and Kay, S. A. (2012) Identification of small molecule activators of cryptochrome. Science 337, 1094-1097.

Isojima, Y., Nakajima, M., Ukai, H., Fujishima, H., Yamada, R. G., Masumoto, K. H., Kiuchi, R., Ishida, M., Ukai-Tadenuma, M., Minami, Y., Kito, R., Nakao, K., Kishimoto, W., Yoo, S. H., Shimomura, K., Takao, T., Takano, A., Kojima, T., Nagai, K., Sakaki, Y., Takahashi, J. S., and Ueda, H. R. (2009) CKI epsilon/delta-dependent phosphorylation is a temperature-insensitive, period-determining process in the mammalian circadian clock. P Natl Acad Sci USA 106, 15744-15749.

Chun, S. K., Jang, J., Chung, S., Yun, H., Kim, N. J., Jung, J. W., Son, G. H., Suh, Y. G., and Kim, K. (2014) Identification and Validation of Cryptochrome Inhibitors That Modulate the Molecular Circadian Clock (vol 9, pg 703, 2014). Acs Chem Biol 9, 1213-1213.

Hu, Y., Spengler, M. L., Kuropatwinski, K. K., Comas, M., Jackson, M., Chernov, M. V., Gleiberman, A. S., Fedtsova, N., Rustum, Y. M., Gudkov, A. V., and Antoch, M. P. (2011) Selenium is a modulator of circadian clock that protects mice from the toxicity of a chemotherapeutic drug via upregulation of the core clock protein, BMAL1. Oncotarget 2, 1279-1290.

Huang, N., Chelliah, Y., Shan, Y., Taylor, C. A., Yoo, S. H., Partch, C., Green, C. B., Zhang, H., and Takahashi, J. S. (2012) Crystal structure of the heterodimeric CLOCK: BMAL1 transcriptional activator complex. Science 337, 189-194.

Dubrovsky Y V, Samsa W E, Kondratov R V. Deficiency of circadian protein CLOCK reduces lifespan and increases age-related cataract development in mice. Aging (Albany NY). 2010; 2 (12): 936-944.

McIntosh, B. E., Hogenesch, J. B., and Bradfield, C. A. (2010) Mammalian Per-Arnt-Sim proteins in environmental adaptation. Annu Rev Physiol 72, 625-645.

Phillips, J. C., Braun, R., Wang, W., Gumbart, J., Tajkhorshid, E., Villa, E., Chipot, C., Skeel, R. D., Kale, L., and Schulten, K. (2005) Scalable molecular dynamics with NAMD. J Comput Chem 26, 1781-1802

Humphrey, W., Dalke, A., and Schulten, K. (1996). VMD: visual molecular dynamics. J Mol Graph 14, 33-38, 27-38.

Morris, G. M., Huey, R., Lindstrom, W., Sanner, M. F., Belew, R. K., Goodsell, D. S., and Olson, A. J. (2009). AutoDock4 and AutoDockTools4: Automated docking with selective receptor flexibility. J Comput Chem 30, 2785-2791.

Lipinski, C. A. (2000). Drug-like properties and the causes of poor solubility and poor permeability. J Pharmacol Toxicol Methods 44, 235-249.

McClung, C. A. (2007). Clock genes and bipolar disorder: implications for therapy. Pharmacogenomics 8, 1097-1100.

Vitaterna, M. H., Ko, C. H., Chang, A. M., Buhr, E. D., Fruechte, E. M., Schook, A., Antoch, M. P., Turek, F. W., and Takahashi, J. S. (2006). The mouse Clock mutation reduces circadian pacemaker amplitude and enhances efficacy of resetting stimuli and phase-response curve amplitude. Proc Natl Acad Sci USA 103, 9327-9332.

Nievergelt C. M., Kripke D. F., Barrett T. B., Burg E., Remick R. A., Sadovnick A. D. Suggestive evidence for association of the circadian genes PERIOD3 and ARNTL with bipolar disorder. Am. J. Med. Genet. B Neuropsychiatr. Genet. 2006; 141B: 234-241.

Mansour H. A., Wood J., Logue T., Chowdari K. V., Dayal M., Kupfer D. J., Monk T. H., Devlin B., Nimgaonkar V. L. Association study of eight circadian genes with bipolar I disorder, schizoaffective disorder and schizophrenia. Genes Brain Behav. 2006; 5:150-157.

Kondratov, R. V., Chernov, M. V., Kondratova, A. A., Gorbacheva, V. Y., Gudkov, A. V., and Antoch, M. P. (2003). BMAL1-dependent circadian oscillation of nuclear CLOCK: posttranslational events induced by dimerization of transcriptional activators of the mammalian clock system. Genes Dev 17, 1921-1932.

What is claimed is:

1. A method for a treatment of a disease or a disorder associated with circadian rhythm in a subject in need thereof, comprising administering to the subject a therapeutically effective amount of a compound having the following formula or a pharmaceutically acceptable salt of the compound:

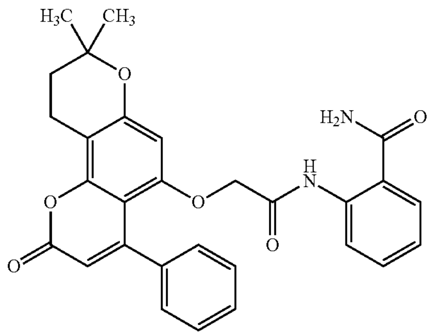 [SMILES: CC1(C)CCc2c(cc(OCC(=O)Nc3ccccc3C(N)=O)c3c(-c4ccccc4)cc(=O)oc23)O1]

wherein the disease or the disorder is a sleep disorder.

2. The method according to claim 1, wherein the compound has an inhibition of CLOCK:BMAL1 interaction.

3. The method according to claim 1, wherein the sleep disorder is a circadian rhythm sleep disorder selected from the group consisting of a shift work sleep disorder, a jet lag syndrome, an advanced sleep phase syndrome, a non-24-hour sleep-wake syndrome, an irregular sleep-wake rhythm, and a delayed sleep phase syndrome.

* * * * *

SEQUENCE LISTING

```
<160> NUMBER OF SEQ ID NOS: 6

<210> SEQ ID NO 1
<211> LENGTH: 2540
<212> TYPE: DNA
<213> ORGANISM: Artificial Sequence
<220> FEATURE:
<223> OTHER INFORMATION: Homo Sapiens

<400> SEQUENCE: 1

atgttgttta ccgtaagctg tagtaaaatg agctcgattg ttgacagaga tgacagtagt      60
```

-continued

```
atttttgatg ggttggtgga agaagatgac aaggacaaag cgaaaagagt atctagaaac    120
aaatctgaaa agaaacgtag agatcaattt aatgttctca ttaaagaact gggatccatg    180
cttcctggta atgctagaaa gatggacaaa tctactgttc tgcagaaaag cattgatttt    240
ttacgaaaac ataaagaaat cactgcacag tcagatgcta gtgaaattcg acaggactgg    300
aaacctacat tccttagtaa tgaagagttt acacaattaa tgttagaggc tcttgatggt    360
tttttttttag caatcatgac agatggaagc ataatatatg tgtctgagag tgtaacttca    420
ttacttgaac atttaccatc tgatcttgtg gatcaaagta tatttaattt tatcccagaa    480
ggggaacatt cagaggttta taaaatactc tctactcatc tgctggaaag tgattcatta    540
accccagaat atttaaaatc aaaaaatcag ttagaattct gttgtcacat gctgcgagga    600
acaatagacc caaaggagcc atctacctat gaatatgtaa aatttatagg aaatttcaaa    660
tctttaaaca gtgtatcctc ttcagcacac aatggttttg aaggaactat acaacgcaca    720
cataggccat cttatgaaga tagagtttgt tttgtagcta ctgtcaggtt agctacacct    780
cagttcatca aggaaatgtg cactgttgaa gaacccaatg aagagtttac atctagacat    840
agtttagaat ggaagtttct gtttctagat cacagggcac cacccataat agggtatttg    900
ccatttgaag ttctgggaac atcaggctat gattactatc atgtggatga cctagaaaat    960
ttggcaaaat gtcatgagca cttaatgcaa tatgggaaag gcaaatcatg ttattatagg   1020
ttcctgacta aggggcaaca gtggatttgg cttcagactc attattatat cacttaccat   1080
cagtggaatt caaggccaga gtttattgtt tgtactcaca ctgtagtaag ttatgcagaa   1140
gttagggctg aaagacgacg agaacttggc atgaagagtc tcttcctgag acagctgctg   1200
acaaaagcca agattctggg tcagataatc gtataaacac agtcagtctc aaggaagcat   1260
tggaaaggtt tgatcacagc ccaacccctt ctgcctcttc tcggagttca agaaaatcat   1320
ctcacacggc cgtctcagac ccttcctcaa caccaaccaa gatcccgacg gatacgagca   1380
ctccacccag gcagcattta ccagctcatg agaagatggt gcaaagaagg tcatcattta   1440
gtagtcagtc cataaattcc cagtctgttg gttcatcatt aacacagcca gtgatgtctc   1500
aagctacaaa tttaccaatt ccacaaggca tgtcccagtt tcagttttca gctcaattag   1560
gagccatgca acatctgaaa gaccaattgg aacaacggac acgcatgata gaagcaaata   1620
ttcatcggca acaagaagaa ctaagaaaaa ttcaagaaca acttcagatg gtccatggtc   1680
aggggctgca gatgtttttg caacaatcaa atcctgggtt gaattttggt tccgttcaac   1740
tttcttctgg aaattcatct aacatccagc aacttgcacc tataaatatg caaggccaag   1800
ttgttcctac taaccagatt caaagtggaa tgaatactgg acacattggc acaactcagc   1860
acatgataca acaacagact ttacagagta catcaactca gagtcaacaa aatgtactga   1920
gtgggcacag tcagcaaaca tctctaccca gtcagacaca gagcactctt acagccccac   1980
tgtataacac tatggtgatt tctcagcctg cagccggaag catggtccag attccatcta   2040
gtatgccaca aaacagcacc cagagtgctg cagtaactac attcactcag gacaggcaga   2100
taagattttc tcaaggtcaa caacttgtga ccaaattagt gactgctcct gtagcttgtg   2160
gggcagtcat ggtacctagt actatgctta tgggccaggt ggtgactgca tatcctactt   2220
ttgctacaca acagcaacag tcacagacat tgtcagtaac gcagcagcag cagcagcaga   2280
gctcccagga gcagcagctc acttcagttc agcaaccatc tcaggctcag ctgacccagc   2340
caccgcaaca atttttacag acttctaggt tgctccatgg gaatccctca actcaactca   2400
```

-continued

```
ttctctctgc tgcatttcct ctacaacaga gcaccttccc tcagtcacat caccagcaac   2460

atcagtctca gcaacagcag caactcagcc ggcacaggac tgacagcttg cccgaccctt   2520

ccaaggttca accacagtag                                                2540


<210> SEQ ID NO 2
<211> LENGTH: 846
<212> TYPE: PRT
<213> ORGANISM: Artificial Sequence
<220> FEATURE:
<223> OTHER INFORMATION: Homo Sapiens

<400> SEQUENCE: 2

Met Leu Phe Thr Val Ser Cys Ser Lys Met Ser Ser Ile Val Asp Arg
1               5                   10                  15

Asp Asp Ser Ser Ile Phe Asp Gly Leu Val Glu Glu Asp Asp Lys Asp
            20                  25                  30

Lys Ala Lys Arg Val Ser Arg Asn Lys Ser Glu Lys Lys Arg Arg Asp
        35                  40                  45

Gln Phe Asn Val Leu Ile Lys Glu Leu Gly Ser Met Leu Pro Gly Asn
    50                  55                  60

Ala Arg Lys Met Asp Lys Ser Thr Val Leu Gln Lys Ser Ile Asp Phe
65                  70                  75                  80

Leu Arg Lys His Lys Glu Ile Thr Ala Gln Ser Asp Ala Ser Glu Ile
                85                  90                  95

Arg Gln Asp Trp Lys Pro Thr Phe Leu Ser Asn Glu Glu Phe Thr Gln
            100                 105                 110

Leu Met Leu Glu Ala Leu Asp Gly Phe Phe Leu Ala Ile Met Thr Asp
        115                 120                 125

Gly Ser Ile Ile Tyr Val Ser Glu Ser Val Thr Ser Leu Leu Glu His
    130                 135                 140

Leu Pro Ser Asp Leu Val Asp Gln Ser Ile Phe Asn Phe Ile Pro Glu
145                 150                 155                 160

Gly Glu His Ser Glu Val Tyr Lys Ile Leu Ser Thr His Leu Leu Glu
                165                 170                 175

Ser Asp Ser Leu Thr Pro Glu Tyr Leu Lys Ser Lys Asn Gln Leu Glu
            180                 185                 190

Phe Cys Cys His Met Leu Arg Gly Thr Ile Asp Pro Lys Glu Pro Ser
        195                 200                 205

Thr Tyr Glu Tyr Val Lys Phe Ile Gly Asn Phe Lys Ser Leu Asn Ser
    210                 215                 220

Val Ser Ser Ser Ala His Asn Gly Phe Glu Gly Thr Ile Gln Arg Thr
225                 230                 235                 240

His Arg Pro Ser Tyr Glu Asp Arg Val Cys Phe Val Ala Thr Val Arg
                245                 250                 255

Leu Ala Thr Pro Gln Phe Ile Lys Glu Met Cys Thr Val Glu Glu Pro
            260                 265                 270

Asn Glu Glu Phe Thr Ser Arg His Ser Leu Glu Trp Lys Phe Leu Phe
        275                 280                 285

Leu Asp His Arg Ala Pro Pro Ile Ile Gly Tyr Leu Pro Phe Glu Val
    290                 295                 300

Leu Gly Thr Ser Gly Tyr Asp Tyr Tyr His Val Asp Asp Leu Glu Asn
305                 310                 315                 320

Leu Ala Lys Cys His Glu His Leu Met Gln Tyr Gly Lys Gly Lys Ser
                325                 330                 335
```

-continued

```
Cys Tyr Tyr Arg Phe Leu Thr Lys Gly Gln Gln Trp Ile Trp Leu Gln
            340                 345                 350

Thr His Tyr Tyr Ile Thr Tyr His Gln Trp Asn Ser Arg Pro Glu Phe
        355                 360                 365

Ile Val Cys Thr His Thr Val Val Ser Tyr Ala Glu Val Arg Ala Glu
    370                 375                 380

Arg Arg Arg Glu Leu Gly Ile Glu Glu Ser Leu Pro Glu Thr Ala Ala
385                 390                 395                 400

Asp Lys Ser Gln Asp Ser Gly Ser Asp Asn Arg Ile Asn Thr Val Ser
                405                 410                 415

Leu Lys Glu Ala Leu Glu Arg Phe Asp His Ser Pro Thr Pro Ser Ala
            420                 425                 430

Ser Ser Arg Ser Ser Arg Lys Ser Ser His Thr Ala Val Ser Asp Pro
        435                 440                 445

Ser Ser Thr Pro Thr Lys Ile Pro Thr Asp Thr Ser Thr Pro Pro Arg
    450                 455                 460

Gln His Leu Pro Ala His Glu Lys Met Val Gln Arg Arg Ser Ser Phe
465                 470                 475                 480

Ser Ser Gln Ser Ile Asn Ser Gln Ser Val Gly Ser Ser Leu Thr Gln
                485                 490                 495

Pro Val Met Ser Gln Ala Thr Asn Leu Pro Ile Pro Gln Gly Met Ser
            500                 505                 510

Gln Phe Gln Phe Ser Ala Gln Leu Gly Ala Met Gln His Leu Lys Asp
        515                 520                 525

Gln Leu Glu Gln Arg Thr Arg Met Ile Glu Ala Asn Ile His Arg Gln
    530                 535                 540

Gln Glu Glu Leu Arg Lys Ile Gln Glu Gln Leu Gln Met Val His Gly
545                 550                 555                 560

Gln Gly Leu Gln Met Phe Leu Gln Gln Ser Asn Pro Gly Leu Asn Phe
                565                 570                 575

Gly Ser Val Gln Leu Ser Ser Gly Asn Ser Ser Asn Ile Gln Gln Leu
            580                 585                 590

Ala Pro Ile Asn Met Gln Gly Gln Val Val Pro Thr Asn Gln Ile Gln
        595                 600                 605

Ser Gly Met Asn Thr Gly His Ile Gly Thr Thr Gln His Met Ile Gln
    610                 615                 620

Gln Gln Thr Leu Gln Ser Thr Ser Thr Gln Ser Gln Gln Asn Val Leu
625                 630                 635                 640

Ser Gly His Ser Gln Gln Thr Ser Leu Pro Ser Gln Thr Gln Ser Thr
                645                 650                 655

Leu Thr Ala Pro Leu Tyr Asn Thr Met Val Ile Ser Gln Pro Ala Ala
            660                 665                 670

Gly Ser Met Val Gln Ile Pro Ser Ser Met Pro Gln Asn Ser Thr Gln
        675                 680                 685

Ser Ala Ala Val Thr Thr Phe Thr Gln Asp Arg Gln Ile Arg Phe Ser
    690                 695                 700

Gln Gly Gln Gln Leu Val Thr Lys Leu Val Thr Ala Pro Val Ala Cys
705                 710                 715                 720

Gly Ala Val Met Val Pro Ser Thr Met Leu Met Gly Gln Val Val Thr
                725                 730                 735

Ala Tyr Pro Thr Phe Ala Thr Gln Gln Gln Gln Ser Gln Thr Leu Ser
            740                 745                 750

Val Thr Gln Gln Gln Gln Gln Gln Ser Ser Gln Glu Gln Gln Leu Thr
```

-continued

```
        755                 760                 765

Ser Val Gln Gln Pro Ser Gln Ala Gln Leu Thr Gln Pro Pro Gln Gln
    770                 775                 780

Phe Leu Gln Thr Ser Arg Leu Leu His Gly Asn Pro Ser Thr Gln Leu
785                 790                 795                 800

Ile Leu Ser Ala Ala Phe Pro Leu Gln Gln Ser Thr Phe Pro Gln Ser
                805                 810                 815

His His Gln Gln His Gln Ser Gln Gln Gln Gln Gln Leu Ser Arg His
            820                 825                 830

Arg Thr Asp Ser Leu Pro Asp Pro Ser Lys Val Gln Pro Gln
        835                 840                 845


<210> SEQ ID NO 3
<211> LENGTH: 47
<212> TYPE: DNA
<213> ORGANISM: Artificial Sequence
<220> FEATURE:
<223> OTHER INFORMATION: Oligonucleotid primer

<400> SEQUENCE: 3

cagaaaagca ttgatgcttt acgaaaacat aaagaaatca ctgcaca                   47


<210> SEQ ID NO 4
<211> LENGTH: 48
<212> TYPE: DNA
<213> ORGANISM: Artificial Sequence
<220> FEATURE:
<223> OTHER INFORMATION: Oligonucleotid primer

<400> SEQUENCE: 4

ctgtgcagtg atttctttat gttttcgtaa agcatcaatg cttttctg                  48


<210> SEQ ID NO 5
<211> LENGTH: 42
<212> TYPE: DNA
<213> ORGANISM: Artificial Sequence
<220> FEATURE:
<223> OTHER INFORMATION: Oligonucleotid primer

<400> SEQUENCE: 5

gtaaaattta taggaaattt cgcatcttta aacagtgtat cc                        42


<210> SEQ ID NO 6
<211> LENGTH: 42
<212> TYPE: DNA
<213> ORGANISM: Artificial Sequence
<220> FEATURE:
<223> OTHER INFORMATION: Oligonucleotid primer

<400> SEQUENCE: 6

ggatacactg tttaaagatg cgaaatttcc tataaatttt ac                        42
```